United States Patent [19]
Kimura et al.

[11] Patent Number: 6,090,804
[45] Date of Patent: Jul. 18, 2000

[54] THIOPHENE DERIVATIVE AND PHARMACEUTICAL COMPOSITION THEREOF

[75] Inventors: Takenori Kimura; Takeshi Murakami; Junya Ohmori; Takuma Morita; Shin-ichi Tsukamoto, all of Ibaraki, Japan

[73] Assignee: Yamanouchi Pharmaceutical Co., Ltd., Tokyo, Japan

[21] Appl. No.: 09/214,228

[22] PCT Filed: Jun. 30, 1997

[86] PCT No.: PCT/JP97/02255

§ 371 Date: Dec. 30, 1998

§ 102(e) Date: Dec. 30, 1998

[87] PCT Pub. No.: WO98/00420

PCT Pub. Date: Jan. 8, 1998

[30] Foreign Application Priority Data

Jul. 1, 1996 [JP] Japan .................................. 8-170970

[51] Int. Cl.[7] ........................ A61K 31/55; C07D 403/00; C07D 405/00

[52] U.S. Cl. ........................... 514/212; 540/603; 540/596

[58] Field of Search ....................... 514/212, 383, 514/364; 540/603, 596; 548/265.6, 266.2, 143

[56] References Cited

U.S. PATENT DOCUMENTS

| | | | |
|---|---|---|---|
| 4,667,033 | 5/1987 | Hilboll et al. | 544/114 |
| 4,820,834 | 4/1989 | Evans et al. | 540/504 |
| 4,904,653 | 2/1990 | Clark et al. | 514/215 |
| 5,332,732 | 7/1994 | Scott et al. | 514/212 |
| 5,571,810 | 11/1996 | Matsuo et al. | 514/231.5 |
| 5,658,923 | 8/1997 | Takahashi et al. | 514/299 |
| 5,760,032 | 6/1998 | Kitajima et al. | 514/220 |

FOREIGN PATENT DOCUMENTS 0 696 586 A1  2/1996  European Pat. Off. .

OTHER PUBLICATIONS

Matsumoto et al, "Composite organic electrophotographic photoconductors", CA108:195892, 1988.

Franz, E., "Synthesis and Solvatochromic Properties of Donor–Acceptor–Substituted Oligothiophenes", J. Org. Chem., vol. 60, No. 7, (1995), pp. 2082–2091, particularly p. 2084, scheme 3.

*Primary Examiner*—Deborah C. Lambkin
*Attorney, Agent, or Firm*—Sughrue, Mion, Zinn, Macpeak & Seas, PLLC

[57] ABSTRACT

Thiophene derivatives represented by the following general formula (I) or pharmaceutically acceptable salts thereof. Said compounds act as an anti-PCP agonist and therefore are useful as psychotropic or antischizophrenic agents and so on.

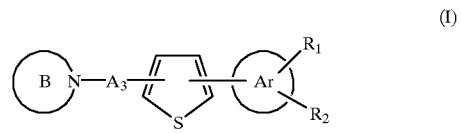

(I)

(In the above formula, $R_1$ is a formula $-A_1-X_1-R_3$; $R_2$ is a formula $-A_2-X_2-R_4$ or does not exist; B ring is a 7- to 10-membered nitrogen-containing cycloalkyl ring; Ar ring is an aryl or heteroaryl ring; $A_1$, $A_2$ and $A_3$ may be the same or different from one another and each represents a bond or a lower alkylene group; $X_1$ and $X_2$ may be the same or different from each other and each represents a bond or a formula $-O-$, $-S-$ or the like; $R_3$ and $R_4$ may be the same or different from each other and each represents a hydrogen atom, a cyclic imido group or a lower alkyl group, a cycloalkyl group, an aryl group or an aralkyl group; with the proviso that, when Ar ring is thiazole ring, either one of $A_1$ and $A_2$ is a lower alkylene group. Also, when Ar ring is a benzene ring, a case in which one of $R_1$ and $R_2$ is methyl group or a halogen group and the other is a hydrogen atom is excluded.)

11 Claims, No Drawings

THIOPHENE DERIVATIVE AND PHARMACEUTICAL COMPOSITION THEREOF

This application is a 371 of PCT/JP97/02255 Oct. 30, 1997.

TECHNICAL FIELD

This invention relates to medicaments, particularly to a novel thiophene derivative having an anti-PCP (phencyclidine) action or a pharmaceutically acceptable salt thereof and to an anti-PCP agonist which comprises said derivative as an active ingredient.

BACKGROUND ART

It is known that PCP induces mental symptoms which resemble closely to various symptoms of schizophrenia, including negative symptoms [Am. J. Psychiat., 135, 1081 (1987); Am. J. Psychiat., 148, 1301 (1991)]. On the other hand, various types of abnormal behavior are induced when PCP is administered to animals. Accordingly, it is considered that a drug which specifically inhibits the PCP-induced abnormal behavior of animals (anti-PCP action) are useful as an agent for the treatment of schizophrenia in humans [Shinkei Seishin Yakuri (nervous and mental pharmacology), 15 (10), 651 (1993); Behav. Brain Res., 74, 45 (1996)]. In addition, since PCP has an NMDA receptor inhibition action [J. Pharm. Exp. Thera., 238, 938 (1986); Br. J. Pharmacol., 79, 565 (1982)], it is considered that such agents having anti-PCP actions are also useful as agents for the treatment of diseases caused by the reduction of NMDA receptor functions, namely disturbance of memory or cognition, delirium or the like problematic behavior in senile dementia [J. Neurochem., 54 (2), 526 (1990); Life Science, 55 (25/26), 2147 (1994)].

Dopamine receptor blockers have hitherto been used mainly as agents for the treatment of schizophrenia. However, these dopamine blockers have problems in that they show less effects for negative symptoms and generate extrapyramidal symptoms and the like side effects [T. I. P. S., 13, 116 (1992)].

On the contrary, specific anti-PCP agents are excellent in terms of the facts that they can improve negative symptoms of schizophrenia, for which dopamine blockers are not effective, and do not cause the side effects like the case of dopamine blockers.

Previously, the inventors of the present invention have found that a novel thiophene derivative having a nitrogen-containing cycloalkyl lower alkyl group has an anti-PCP action and have reported the results in WO 94/225450 or WO 95/22910.

On the other hand, JP-A-62-192379 discloses a compound represented by the following general formula

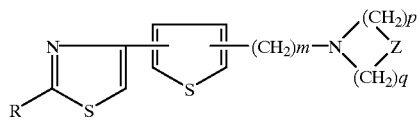

(see this published application for detailed definitions), which will become a thiophene derivative having a nitrogen-containing cycloalkyl group and a thiazole group, depending on the selection of substituents. Similar compounds are also described in JP-A-61-18178. According to the descriptions in both of these published applications, these compounds have anti-hypoxic action, anti-amnestic action and anti-anxiety action and are useful also as antidementia agents or anxiolytic agents. However, they do not disclose about anti-PCP actions.

In addition, Journal of the Chemical Society, Perkin Transactions Pt.1: Organic Chemistry, 22, 2355 (1976) describes a method for the synthesis of a compound represented by the following general formula

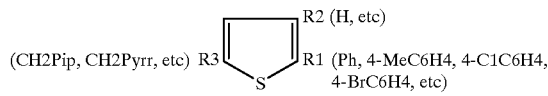

(see the literature for detailed definitions), but it also does not suggest or disclose about anti-PCP actions.

The novel thiophene derivative of the present invention represented by the general formula (I) excludes the compounds described in the aforementioned Japanese published applications and literature and is clearly different from the compound disclosed by the present inventors in the aforementioned international publication pamphlet in terms of their structures.

DISCLOSURE OF THE INVENTION

The inventors of the present invention have conducted extensive studies on compounds having specific and excellent anti-PCP actions and, as a result, found that a thiophene derivative having a nitrogen-containing cycloalkyl lower alkyl group (or a nitrogen-containing unsaturated heterocycle) and an aryl ring or an aromatic heterocycle or a pharmaceutically acceptable salt thereof has excellent anti-PCP actions, thus resulting in the accomplishment of the present invention.

Accordingly, the present invention is a novel thiophene derivative represented by the following general formula (I) or a pharmaceutically acceptable salt thereof

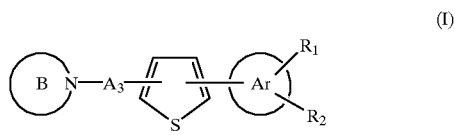

(each symbol in the above formula means as follows, $R_1$: formula $—A_1—X_1—R_3$,
$R_2$: formula $—A_2—X_2—R_4$ or does not exist,
ring:
  1) 4- to 10-membered nitrogen-containing cycloalkyl ring, or
  2) 5- or 6-membered nitrogen-containing unsaturated heterocycle,
Ar ring: an aryl ring which may have a substituent, or a 5- or 6-membered aromatic heterocycle or an 8- to 10-membered aromatic bicyclic heterocycle, which contains 1 to 4 of one or more types of hetero atoms selected from the group consisting of a nitrogen atom, an oxygen atom and a sulfur atom,
$A_1$, $A_2$ and $A_3$: the same or different from one another, and each represents a bond or a lower alkylene group,
$X_1$ and $X_2$: the same or different from each other, and each represents a bond or a formula $—O—$, $—S—$, $—NR_5—$,

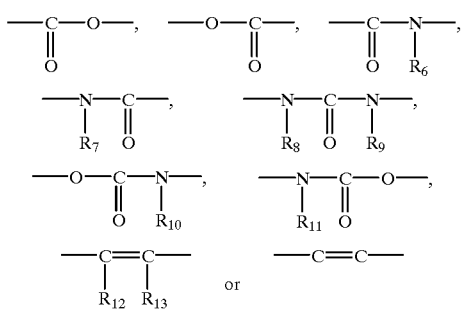

$R_5$, $R_6$, $R_7$, $R_8$, $R_9$, $R_{10}$, $R_{11}$, $R_{12}$ and $R_{13}$: the same or different from one another, and each represents a hydrogen atom or a lower alkyl group, and $R_3$ and $R_4$: the same or different from each other, and each represents a hydrogen atom, a cyclic imido group which may have a substituent and may be condensed with a benzene ring, or a lower alkyl group, a cycloalkyl group, an aryl group or an aralkyl group, which may respectively have a substituent, with the proviso that, when Ar ring is thiazole ring, either one of $A_1$ and $A_2$ is a lower alkylene group, when Ar ring is a thiophene ring, at least one of $R_3$ and $R_4$ is a group other than a hydrogen atom, and when Ar ring is a benzene ring, those in which $R_1$ and $R_2$ is methyl group or a halogen group and the other is a hydrogen atom is excluded).

Another object of the present invention is to provide a pharmaceutical composition which comprises the just described thiophene derivative (I) or a pharmaceutically acceptable salt thereof and a pharmaceutically acceptable carrier. In addition, said pharmaceutical composition is an anti-PCP agonist.

Preferably, the just described anti-PCP agonist is a psychotropic agent or an antischizophrenic agent. Also, the anti-PCP agonist is a drug for use in the treatment of diseases caused by the functional reduction of NMDA receptors, namely a drug for preventing dementia, a drug for improving problematic behavior accompanied by dementia, a drug for treating mental retardation in childhood and/or a drug for treating autism.

The thiophene derivative of the present invention represented by the general formula (I) or a pharmaceutically acceptable salt thereof has a characteristic feature in terms of its chemical structure, namely it is a thiophene derivative substituted with a nitrogen-containing cycloalkyl lower alkyl group (or a nitrogen-containing unsaturated heterocyclic group-substituted lower alkyl group) and an aryl ring or an aromatic heterocycle, and has a pharmacological characteristic in terms of the fact that it can improve negative symptoms of schizophrenia, which cannot be effected by dopamine receptor blockers.

The thiophene derivative represented by the general formula (I) or a pharmaceutically acceptable salt thereof is not described in any of the aforementioned patents and literature, so that it is a novel compound capable of exerting new effects which are not described in said patents and the like.

In other words, the compounds described in the aforementioned patents and literature are definitely excluded from the compound (I) of the present invention in terms of the definition of the substituents $R_1$ and $R_2$ of the Ar ring.

The following describes the compound of the present invention in detail.

In the definition of the general formula of the present invention, the term "lower" means a straight or branched carbon chain having 1 to 6 carbon atoms unless otherwise noted.

Thus, illustrative examples of the "lower alkyl group" include a methyl group, an ethyl group, a propyl group, an isopropyl group, a butyl group, an isobutyl group, a sec-butyl group, a tert-butyl group, a pentyl group, an isopentyl group, a neopentyl group, a tertpentyl group, a 1-methylbutyl group, a 2-methylbutyl group, a 1,2-dimethylpropyl group, a hexyl group or an isohexyl group.

Examples of the "lower alkylene group" represented by $A_1$, $A_2$ and $A_3$ include a methylene group, an ethylene group, a methylmethylene group, a trimethylene group, a methylethylene group, a tetramethylene group, a methyltrimethylene group, a pentamethylene group or a hexamethylene group, of which alkylene groups having 1 to 4 carbon atoms are preferred. Among these groups, a methylene group is particularly desirable as the "lower alkylene group" of $A_3$.

The "cycloalkyl group" represented by $R_3$ and $R_4$ is a monocyclic hydrocarbon radical having 3 to 8 ring atoms, and its illustrative examples include a cyclopropyl group, a cyclobutyl group, a cyclopentyl group, a cyclohexyl group, a cycloheptyl group, a cyclooctyl group and the like, of which a cyclohexyl group is desirable.

The "aryl group" is a carbon ring aryl, and its illustrative examples include benzene, biphenyl, naphthalene, anthracene, phenanthrene and the like, of which benzene is preferred.

The "aralkyl group" is a group in which an optional hydrogen atom of the aforementioned "lower alkyl group" is substituted with a phenyl group, a naphthyl group or the like, and its illustrative examples include a benzyl group, a phenetyl group, a phenylpropyl group, a methylphenylethyl group, a phenylbutyl group, a methylphenylpropyl group, an ethylphenylethyl group, a dimethylphenylethyl group, a phenylpentyl group, a methylphenylbutyl group, a phenylhexyl group, a methylphenylpentyl group, a naphthylmethyl group, a naphthylethyl group, a naphthylpropyl group, a naphthylbutyl group, a naphthylpentyl group, a naphthylhexyl group and the like, of which a benzyl group is preferred.

Of the "1) 4- to 10-membered nitrogen-containing cycloalkyl ring, or 2) 5- or 6-membered nitrogen-containing unsaturated heterocycle" represented by the B ring, the "4- to 10-membered nitrogen-containing cycloalkyl ring" is more desirable. Illustrative examples of the "4- to 10-membered nitrogen-containing cycloalkyl ring" include azetidine, pyrrolidine, piperidine, hexahydroazepine, octahydroazosine, octahydroazonine, decahydroxyazesine and the like, of which hexahydroazepine is particularly preferred. The "5- or 6-membered nitrogen-containing unsaturated heterocycle" is a 5- or 6-membered unsaturated ring which contains 1 to 4 nitrogen atoms as hetero atoms, and its illustrative examples include pyrrole, imidazole, triazole, pyrazole, pyridine, pyrazine, pyrimidine, pyridazine, pyrazine, triazi.ne and the like, of which imidazole is preferred.

With regard to the "5- or 6-membered aromatic heterocycle or an 8- to 10-membered aromatic bicyclic heterocycle, which contains 1 to 4 of one or more hetero atoms selected from the group consisting of a nitrogen atom, an oxygen atom and a sulfur atom" represented by the Ar ring, its illustrative examples include pyrrole, imidazole, triazole, furan, oxazole, isoxazole, oxadiazole, thiophene, thiazole, isothiazole, thiadiazole, pyridine, pyridazine, pyrimidine, pyrazine, triazine, indole, isoindole, benzimidazole, benzotriazole, benzofuran, benzoxazole, benzisoxazole, benzoxadiazole, benzothiophene, benzothiazole, benzisothiazole, benzotriadiazole, quinoline, isoquinoline, benzopyridazine, benzopyrimidine, benzopyrazine, benzotriazine, imidazopyridine, imidazopyrimidine, triazopyridazine and the like, of which triazole, oxadiazole, thiazole, thiadiazole, imidazopyridine, imidazopyrimidine and triazolopyridazine are preferred, and triazole and oxadiazole are particularly preferred.

Illustrative examples of the "cyclic imido which may be condensed with a benzene ring" represented by $R_3$ and $R_4$ include succinimido, glutalimido, phthalimido and the like.

Illustrative examples of the "substituent" of the "cyclic imido which may have a substituent and may be condensed with a benzene ring, or a lower alkyl group, a cycloalkyl group, an aryl group or an aralkyl group, which may respectively have a substituent" represented by $R_3$ and $R_4$ include a halogen atom, hydroxyl group, a lower alkoxy group, an acyloxy group, carbamoyloxy group, a mono- or di-lower alkylcarbamoyloxy group, an amino group, a mono- or di-lower alkylamino group, an acylamino group, a carbamoylamino group, a mono- or di-lower alkylcarbamoylamino group, a carboxyl group, a lower alkoxycarbonyl group, a carbamoyl group, a mono- or di-lower alkylcarbamoyl group, a cyano group, nitro group and the like, of which a halogen atom, a nitro group, a hydroxyl group and a lower alkoxy group are preferred.

The "halogen atom" means a fluorine atom, a chlorine atom, a bromine atom or an iodine atom, of which a fluorine atom and a chlorine atom are preferred.

The "lower alkoxy group" is a straight or branched alkoxy group having 1 to 6 carbon atoms, and its illustrative examples include a methoxy group, an ethoxy group, a propoxy group, an isopropoxy group, a butoxy group, an isobutoxy group, a sec-butoxy group, a tert-butoxy group, a pentyloxy group, an isopentyloxy group, a neopentyloxy group, a tert-pentyloxy group and the like, of which a methoxy group is preferred.

The term "acyl" of the "acyloxy group" or "acylamino group" means a lower alkanoyl group or an aroyl group, and its illustrative examples include a formyl group, an acetyl group, a propionyl group, a butyryl group, an isobutyryl group, a valeryl group, an isovaleryl group, a trimethylacetyl group, a hexanoyl group, a tert-butylacetyl group, a benzoyl group, a toluoyl group, an anisoyl group, a naphthalenecarbonyl group and the like.

The compound (I) of the present invention may form acid addition salts in some cases. Examples of such salts include acid addition salts with a mineral acid (e.g., hydrochloric acid, hydrobromic acid, sulfuric acid, nitric acid, phosphoric acid and the like) or with an organic acid (e.g., formic acid, acetic acid, propionic acid, oxalic acid, malonic acid, succinic acid, fumaric acid, maleic acid, lactic acid, malic acid, citric acid, tartaric acid, carbonic acid, picric acid, methanesulfonic acid, ethanesulfonic acid, glutamic acid and the like).

Also, examples of its salts with bases include addition salts with an inorganic base (e.g., lithium, sodium, potassium, magnesium, calcium, aluminum and the like) or an organic base (e.g., methylamine, ethylamine, ethanolamine and the like) and salts with an amino acid (e.g., lysine, ornithine and the like), as well as ammonium salts.

Also, since the compound of the present invention may contain asymmetric carbon atoms in some cases, it may exist in optical isomer forms based thereon. In addition, the compound may exist in diastereomer forms when it has two or more asymmetric carbon atoms. These isomers, either as a mixture thereof or in isolated forms, are all included in the present invention.

Also, the compound (I) of the present invention may be isolated as its hydrates, various solvates (e.g., solvent with ethanol) or their polymorphic crystal forms, and these various kinds of hydrates, solvates and polymorphic substances are also included in the present invention.

Among compounds (I) of the present invention, preferred is a compound in which the B ring is a 4 to 10-membered nitrogen-containing cycloalkyl ring, and more preferable compound is a compound in which the B ring is hexahydroazepine and/or a compound in which $A_3$ is methylene group, further more preferred is a compound in which the Ar ring is triazole, oxadiazole, thiazole, thiadiazole, imidazopyridine, imidazopyrimidine or triazopyridazine, and most preferred is a compound in which the Ar ring is triazole or oxadiazole.

Particularly preferred compound is 5-[5-[(hexahydro-1H-azepin-1-yl)methyl]-2-thienyl]-3-phthalimidoylethyl-1,2,4-oxadiazole, 5-amino-3-[5-[(hexahydro-1H-azepin-1-yl)methyl]-2-thienyl]-1H-1,2,4-triazole or a pharmaceutically acceptable salt thereof.

Thus, compounds of the instant application have been described in detail, and all of them are included in the present invention.

(Production Methods)

The compound (I) of the present invention and pharmaceutically acceptable salts thereof can be produced by applying various synthetic methods making use of the characteristics of the basic nucleus or types of substituents. In that case, it will sometimes be effective from the viewpoint of production techniques to substitute amino and the like of the compound of the present invention with appropriate protecting groups, namely functional groups which can be converted easily into amino and the like. Examples of such protecting groups include, in addition to the aforementioned amino group-protecting groups, those which are described for instance in "Protective Groups in Organic Synthesis", second edition, edited by Green and Wuts, and these groups can be optionally selected and used depending on reaction conditions. In addition to these protecting groups, other functional groups such as nitro and the like which can be converted easily into amino and the like can also be used in the same manner as protecting groups.

The following illustrates typical production method of the compounds of the present invention.

Production Method 1

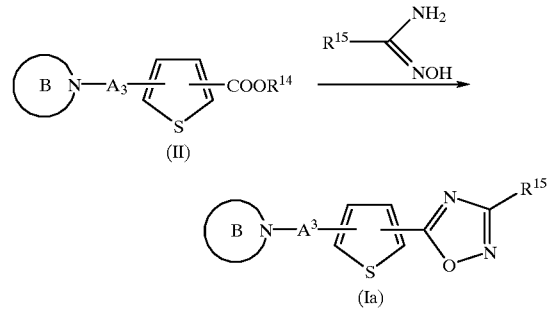

(In the above reaction formula, B ring and $A_3$ are as defined in the foregoing, $R_{14}$ means a lower alkyl group and $R_{15}$ means an amino group or a lower alkyl group having protected hydroxyl group. Examples of the protecting group useful in this case include a benzyl group, a benzhydryl group, a trityl group, an aroyl group, a lower alkanoyl group, a silyl group (e.g., a tert-butyldimethylsilyl group) and an acetal group (e.g., a tetrahydropyranyl group.)

The compound (Ia) of the present invention is produced by allowing an ester compound represented by the general formula (II) to react with an amidoxime compound.

This reaction can be carried out in an organic solvent (e.g., tetrahydrofuran, ether, dioxane or the like) in the presence of a base (e.g., lithium diisopropylamide, lithium bis (trimethylsilyl)amide, sodium hydride or the like) at a temperature of from cooling temperature to heat-reflux temperature.

When $R_{15}$ is protected hydroxyl group, deprotection can be carried out in accordance with usual methods, for example, the protecting group can be removed easily by its reduction or oxidation or its treatment under an acidic condition in the case of a benzyl-based protecting group, by its hydrolysis under an acidic or basic condition in the case of an acyl-based protecting group, by using fluoride ions in the case of a silyl based protecting group or by its treatment under an acidic condition in the case of an acetal based protecting group.

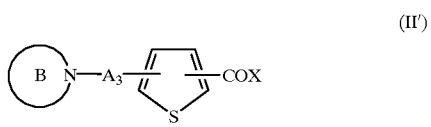

(II')

(In the above formula, B ring and $A_3$ are as defined in the foregoing and X represents a halogen atom.)

Alternatively, the compound of the present invention is produced by allowing a halogenated acyl compound represented by the above general formula (II'), instead of the ester compound of general formula (II), to react with an amidoxime compound. In that case, the reaction can be carried out in a solvent (e.g., tetrahydrofuran, dioxane, chloroform, methylene chloride, benzene, toluene or the like) in the presence of an organic base (e.g., triethylamine, diisopropylethylamine or the like) at room temperature.

Production Method 2

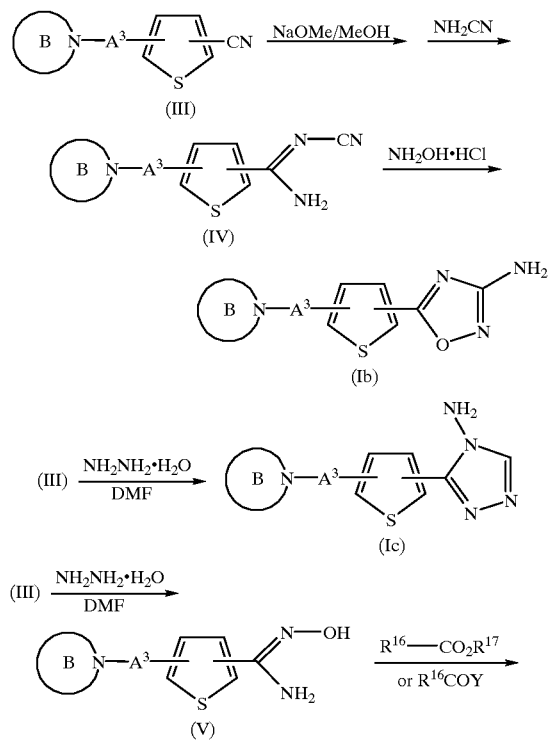

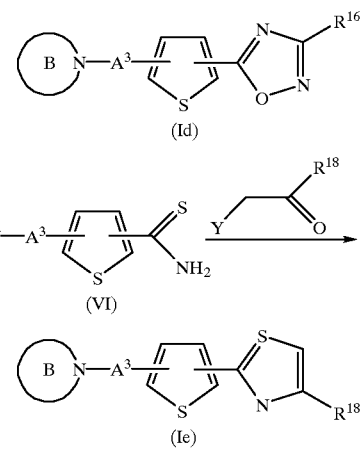

(In the above reaction formula, B ring and $A_3$ are as defined in the foregoing, Y represents a halogen atom, a tosyloxy group, a methyloxy group, a succinimidoxy group or the like leaving group, $R_{16}$ and $R_{18}$ may be the same or different from each other and each represents a protected amino group or a lower alkyl group or an aralkyl group, which may have hydroxyl group, and $R_{17}$ represents a lower alkyl group. The protecting group of this case is as defined in the foregoing.)

The compounds (Ib to e) of the present invention are produced by allowing a nitrile compound represented by the general formula (III) to react with a sodium alkoxide and then with cyanamide to form a cyanoamidine derivative (IV) which is then allowed to react with hydroxylamine hydrochloride, by allowing the compound (III) to react with hydrazine and N,N-dimethylformamide, by allowing (III) to react with hydroxylamine hydrochloride to form an amidoxime derivative (V) which is then allowed to react with an ester compound or an acid anhydride or by allowing (III) to react with hydrogen sulfide to form a thioamide derivative (VI) which is then allowed to react with a ketone derivative.

The reaction with sodium alkoxide can be carried out under a room temperature to heat-reflux condition, and the reaction with cyanamide can be carried out in an organic solvent (e.g., tetrahydrofuran, dioxane or the like) or without solvent. The reaction with hydroxylamine can be carried out at a temperature of from room temperature to heat-reflux temperature using a solvent (e.g., tetrahydrofuran, dioxane, methanol, ethanol or the like) in the presence of an organic base (e.g., triethylamine, diisopropylethylamine or the like) or an inorganic base (e.g., sodium hydroxide, potassium hydroxide or the like). The reaction with hydrazine can be carried out by heat-refluxing using a solvent such as DMF, tetrahydrofuran, dioxane or the like. The reaction with an ester, an acid halide or an acid anhydride can be carried out using a solvent (e.g., tetrahydrofuran, dioxane, chloroform, methylene chloride, benzene, toluene or the like) in the presence of an organic base (e.g., triethylamine, diisopropylethylamine or the like) or an inorganic base (e.g., sodium hydride or the like), or under a neutral condition, at a temperature of from cooling temperature to heat-reflux temperature. The reaction with hydrogen sulfide can be carried out using a solvent (e.g., pyridine, tetrahydrofuran, dioxane or the like) in the presence of an organic base (e.g., triethylamine, diisopropylethylamine or the like). The reaction with a ketone compound can be carried out using a solvent (e.g., methanol, ethanol or the like) at room temperature to heat-reflux temperature.

Production Method 3

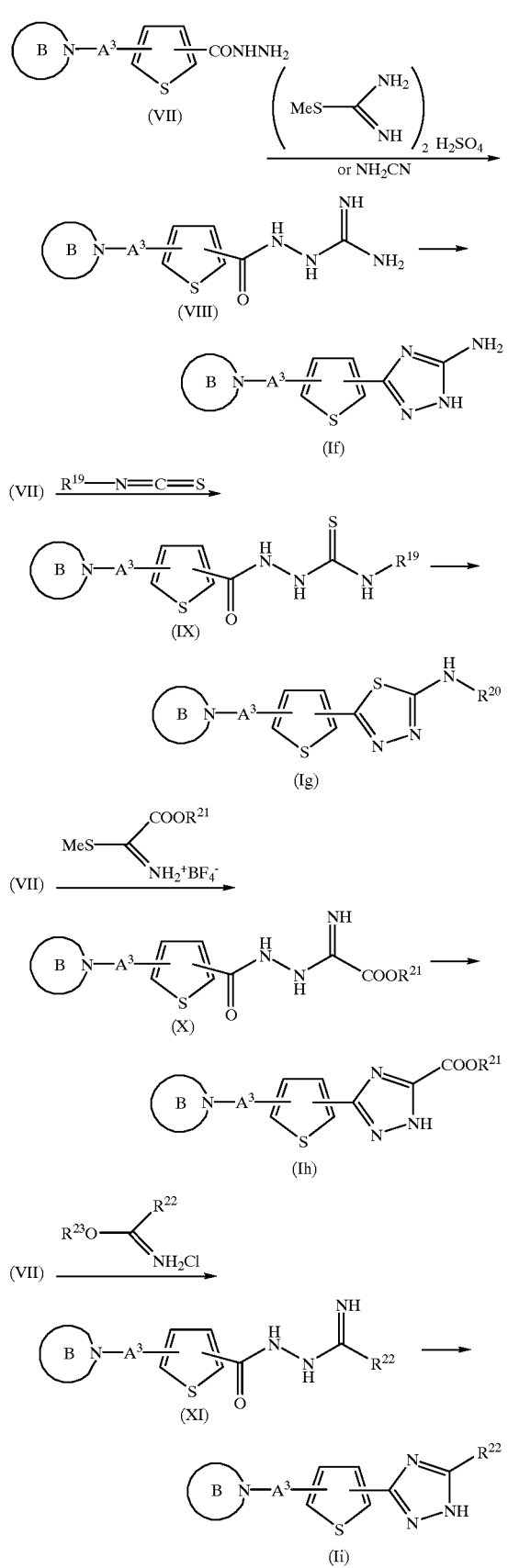

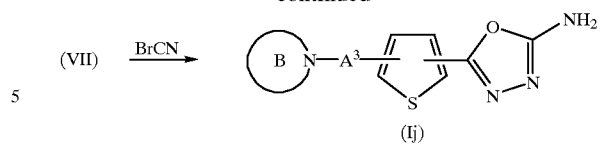

(In the above reaction formula, B ring and $A_3$ are as defined in the foregoing, $R_{19}$ and $R_{22}$ may be the same or different from each other and each represents a lower alkyl group or an aralkyl group, $R_{20}$ represents a hydrogen atom or a lower alkyl group and each of $R_{21}$ and $R_{23}$ represents a lower alkyl group.)

The compounds (If to j) of the present invention are produced by allowing a hydrazide compound represented by the general formula (VII) to react with S-methylisothiourea sulfate, cyanamide, various isothiocyanic acid esters, carbo-lower alkoxy-2-methylformimidium tetrafluoroborate or imidate or an imidate compound and then subjecting to cyclization or by allowing the compound (VII) to react with cyanogen bromide.

The reaction with S-methylisothiourea sulfate or cyanamide can be carried out using a solvent (e.g., methanol, ethanol or the like) at a temperature of from room temperature to heat-reflux temperature, and an inorganic base (e.g., sodium hydroxide, potassium hydroxide or the like) may be used. The reaction with isothiocyanic acid ester can be carried out using a solvent (e.g., methanol, ethanol, THF, dioxane, ether, methylene chloride or the like) at a temperature of from room temperature to heat-reflux temperature. The reaction with carbo-lower alkoxy-2-methylformimidium tetrafluoroborate or an imidate compound can be carried out using a solvent (e.g., THF, dioxane, ether, methylene chloride or the like) in the presence of an organic base (e.g., triethylamine, diisopropylethylamine or the like). The cyclization reaction can be carried out using a solvent (e.g., methanol, ethanol or the like) or without solvent under a neutral condition, under an acidic condition using concentrated sulfuric acid, acetic acid, tosylic acid, trifluoroacetic acid, ammonium chloride or the like or under a basic condition using sodium hydroxide, potassium hydroxide or the like, at a temperature of from room temperature to heat-reflux temperature.

Also, the compound (If) of the present invention can be produced via a compound of the general formula (VIII) by allowing the aforementioned halogenoacyl compound of general formula (II') to react with aminoguanidine.

Production Method 4

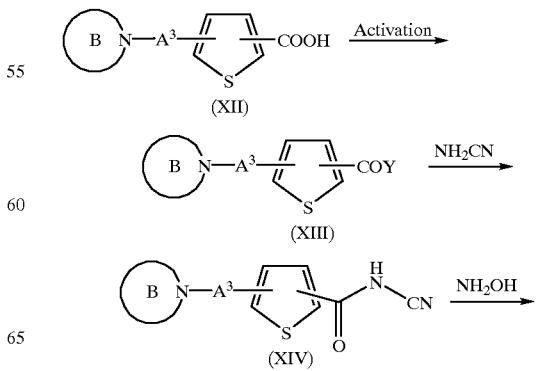

-continued

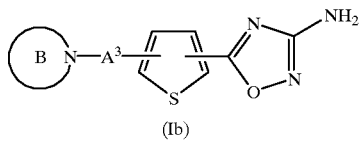

(Ib)

(In the above reaction formula, B ring, $A_3$ and Y are as defined in the foregoing.)

The compound (Ib) of the present invention can be produced by activating a carboxylic acid compound represented by the general formula (XII), allowing the resulting compound to react with cyanamide and then the resulting compound (XIV) to react with hydroxylamine.

The activation can be effected in the usual way to convert the compound into a halide, acid anhydride or succinimide ester. Reaction of the activated acid derivative (XIII) with cyanamide can be carried out using an organic base (e.g., tetrahydrofuran, dioxane, chloroform, methylene chloride, benzene, toluene or the like) in the presence of an organic base (e.g., triethylamine, diisopropylethylamine or the like) or an inorganic base (e.g., sodium hydride or the like). The reaction with hydroxylamine can be carried out under the same conditions of the production method 2.

Production Method 5

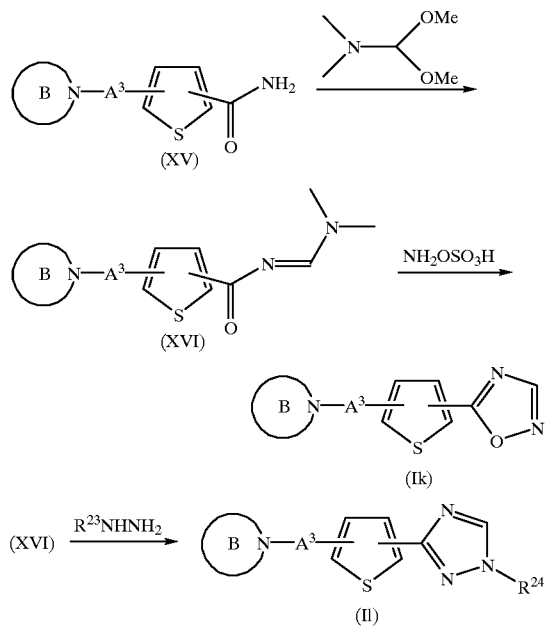

(In the above reaction formula, B ring and $A_3$ are as defined in the foregoing and each of $R_{23}$ and $R_{24}$ is a lower alkyl group.)

Compounds (Ik and Il) of the present invention can be produced by allowing an acid amide derivative represented by the general formula (XV) to react with N,N-dimethylformamidomethylacetal and cyanamide and the allowing the resulting compound (XVI) to react with hydroxylamine-o-sulfonic acid or a hydrazine compound.

The reaction with N,N-dimethylformamidomethylacetal can be carried out at room temperature or with heating, using DMF as the solvent. The reaction with hydroxylamine-o-sulfonic acid can be carried out in an organic base (e.g., methanol, ethanol or the like) in the presence of an organic base (e.g., pyridine, triethylamine, diisopropylethylamine or the like) at a temperature within the range of from room temperature to heat-reflux temperature. The reaction with a hydrazine compound can be carried out using an organic acid (e.g., acetic acid or the like) as the solvent at a temperature within the range of from room temperature to heat-reflux temperature.

Production Method 6

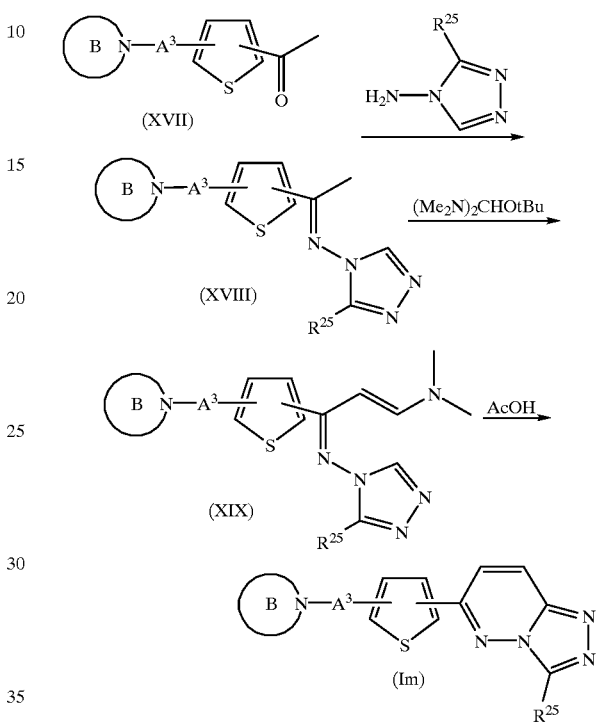

(In the above reaction formula, B ring and $A_3$ are as defined in the foregoing and $R_{25}$ represents a lower alkyl group or aralkyl group.)

A compound (Im) of the present invention can be obtained by allowing an acetyl derivative represented by the general formula (XVII) to react with aminotriazole, allowing the resulting compound to react with tert-butoxybis (dimethylamino)methane and then subjecting the resulting compound (XIX) to cyclization reaction.

The dehydration reaction of aminotriazole can be carried out using a solvent (e.g., benzene, toluene or the like) under an acidic condition using acetic acid, tosylic acid, trifluoroacetic acid or the like, at a temperature within the range of from room temperature to heat-reflux temperature. The cyclization reaction can be carried out under the same conditions of the production method 3.

Production Method 7

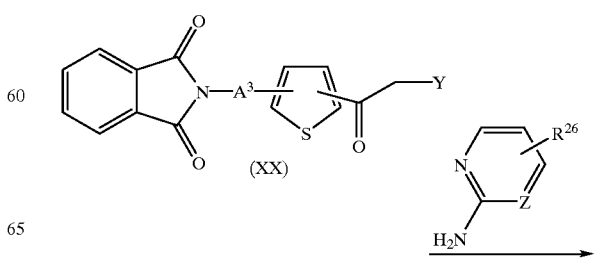

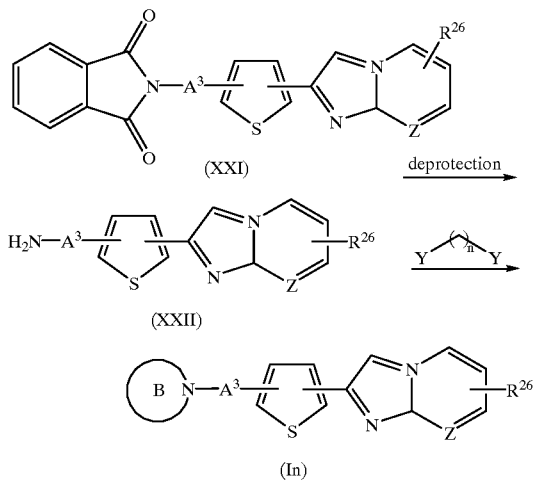

(In the above reaction formula, B ring, $A_3$ and Y are as defined in the foregoing, $R_2$s represents a lower alkyl group or an aralkyl group, Z represents CH or N and n is 3 to 9.)

A compound (In) of the present invention can be produced by allowing a ketone compound represented by the general formula (XX) to react with 2-aminopyridine or 2-aminopyrimidine, removing the phthaloyl group and then forming cyclic amine.

The reaction with 2-aminopyridine or 2-aminopyrimidine can be carried out using a solvent (e.g., methanol, ethanol or the like) at a temperature within the range of from room temperature to heat-reflux temperature. Deprotection of phthaloyl can be carried out in the usual way, for example, by employing a method which uses hydrazine, methylamine or the like. The reaction for the formation of cyclic amine can be effected by employing a usual alkylation reaction of amine. For example, the reaction can be carried out with an alkylene dihalide at a temperature within the range of from room temperature to heat-reflux temperature using a solvent (e.g., propanol, butanol, tetrahydrofuran, dioxane or the like) in the presence of an inorganic base (e.g., potassium carbonate or the like). In this case, potassium iodide or the like may be added in order to accelerate the reaction.

Production Method 8

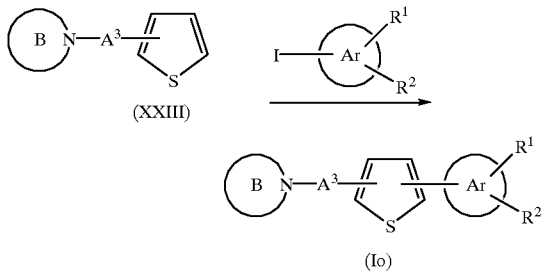

(In the above reaction formula, B ring, $A_3$, Ar, $R_1$ and $R_2$ are as defined in the foregoing.)

A compound (Io) of the present invention can be produced by subjecting a thiophene compound represented by the general formula (XXIII) to metalation reaction and then allowing the resulting compound to react with an iodide compound.

This reaction can be carried out using a solvent (e.g., hexane, tetrahydrofuran, ether, toluene or the like) in the presence of bis(triphenylphosphine)nickel chloride, diisobutylaluminum hydride, n-butyl lithium and zinc chloride at a temperature within the range of from −80° C. to room temperature.

Since compounds (I) of the present invention obtained by the production methods 1 to 8 have various substituents, compounds can also be produced by modifying these groups. For example, a compound having an amino group as a substituent can be modified into its amide, urethane, urea and the like compounds in the usual way, and a compound having ester or carboxyl group as a substituent can be modified into its amide compounds and further into alcohol and the like compounds by reduction in the usual way. In the case of a compound which has hydroxyl group, the hydroxyl group can be converted further into its ester, carbonic ester, urethane and the like compounds in the usual way. Also, the hydroxyl group can be converted into an amino group by subjecting it to Mitsunobu reaction with phthalimide and then deprotecting phthaloyl group under the same conditions as described in the production method Each of the compounds obtained in this manner is isolated and purified as its free form or as a salt thereof, a hydrate thereof, a solvate thereof or a polymorphic substance thereof. Salts of the compound (I) can also be produced by subjecting it to a usually used salt formation reaction.

Its isolation and purification are carried out by applying usual chemical techniques such as extraction, concentration, evaporation, crystallization, filtration, recrystallization, various types of chromatography and the like.

Various isomers can be separated by selecting appropriate material compounds or by making use of a difference in physical properties between isomers. For example, optical isomers can be separated into stereochemically pure isomers by selecting proper materials or by racemic resolution of a racemic compound (for instance, a method in which such a compound is converted into a diastereomer salt with a usual optically active base and then subjected to optical resolution).

INDUSTRIAL APPLICABILITY

Since the compound (I) of the present invention has specific anti-PCP action and can improve reduced NMDA receptor functions, it is useful, based on such effects, as a psychotropic agent, an antischizophrenic agent, an anti-dementia agent for use in Alzheimer disease and the like, an agent for use in improving problematic behavior such as delirium accompanied by dementia and/or an agent for use in the treatment of mental retardation and autism in childhood.

Anti-PCP action of the compound (I) of the present invention has been confirmed by the following test method.

Anti-PCP Action Test

Test Method

PCP (3 mg/kg) was administered to Wistar male rats (n=8) (200 to 300 mg in body weight) by subcutaneous injection, and the rats were put in a hole board apparatus (HBA) 30 minutes thereafter. A test compound (10 mg/kg) was administered by subcutaneous injection 15 minutes before the PCP administration. HBA is an open field of 40 cm in length and breadth, which is surrounded by a wall of 20 cm in height and has a bed having a total of 16 holes of 4 cm in diameter [*Psychopharmacology*, 52, 271 (1977)].

Quantity of motion (locomotion: the number of times moved over 9 partitioned plots) and searching behavior (dipping: the number of times putting the head into holes) of the rats in the HBA were measured for 5 minutes. Also, Wistar male rats (n=8) to which PCP (3 mg/kg) was administered by subcutaneous injection were used as the control group.

In this pharmacological test, the compound of the present invention antagonized PCP-induced increment of the quantity of motion and reduction of the searching behavior with statistical significance (comparison with the control group by Mann-Whitney U-test) (see the following table).

TABLE 1

| Example 34 | Increment of motion quantity | 10 mg/kg · sc | (P < 0.01) |
|---|---|---|---|
| | Reduction of searching behavior | 10 mg/kg · sc | (P < 0.05) |

The pharmaceutical preparation which contains one or two or more of the compounds represented by the general formula (I) or salts thereof as the active ingredient is prepared into tablets, buccals, powders, fine granules, granules, capsules, pills, solutions for oral use (including syrups), injections, inhalations, suppositories, solutions for transdermal use, ointments, adhesive preparations for transdermal use, transmucosal adhesive preparations (e.g., buccal adhesive preparations), solutions for transmucosal use (e.g., solutions for transnasal use) and the like using generally used pharmaceutical carriers, fillers and other additives and administered orally or parenterally.

The solid composition for use in the oral administration according to the present invention is used in the form of tablets, powders, granules and the like, and, in such a solid composition, one or more active substances are mixed with at least one inert diluent such as lactose, mannitol, glucose, hydroxypropylcellulose, microcrystalline cellulose, starch, polyvinyl pyrrolidone or aluminum magnesium silicate. In the usual way, the composition may contain other additives than the inert diluent, such as a lubricant (e.g., magnesium stearate or the like), a disintegrating agent (e.g., calcium cellulose glycolate or the like), a stabilizing agent (e.g., lactose or the like) and a solubilizing or solubilization assisting agent (e.g., glutamic acid, aspartic acid or the like). If necessary, tablets or pills may be coated with a film of a gastric or enteric substance such as sucrose, gelatin, hydroxypropylcellulose, hydroxypropylmethylcellulose phthalate or the like.

The liquid composition for oral administration use includes pharmaceutically acceptable emulsions, solutions, suspensions, syrups, elixirs and the like and contains a generally used inert diluent such as purified water or ethanol. In addition to the inert diluent, this composition may also contain auxiliary agents such as a solubilizing or solubilization assisting agent, a moistening agent, a suspending agent and the like, as well as sweeteners, flavors, aromatics and antiseptics.

The injections for parenteral administration use include aseptic aqueous or non-aqueous solutions, suspensions and emulsions. Examples of the diluent for use in the aqueous solutions and suspensions include distilled water for injection use and physiological saline. Examples of the diluent for use in the non-aqueous solutions and suspensions include propylene glycol, polyethylene glycol, a plant oil (e.g., olive oil or the like), an alcohol (e.g., ethanol or the like), Polysorbate 80 (trade name) and the like. Such a composition may further contain additive agents such as a tonicity agent, an antiseptic agent, a moistening agent, an emulsifying agent, a dispersing agent, a stabilizing agent (e.g., lactose) and a solubilizing or solubilization assisting agent. These compositions are sterilized by filtration through a bacteria retaining filter, blending of a germicide or irradiation. Alternatively, they may be used by firstly making into sterile solid compositions and dissolving them in sterile water or a sterile solvent for injection use prior to their use.

Clinical dose of the compound of the present invention is optionally decided by taking into consideration symptoms, weight, age, sex and the like of each patient to be treated and the route of administration, but is usually from 0.1 to 1,000 mg, preferably from 1 to 200 mg, per day per adult in the case of oral administration, or from 0.1 to 100 mg, preferably from 0.3 to 30 mg, per day per adult in the case of parenteral administration, and the daily dose is used once a day or by dividing it into 2 to 4 doses per day.

BEST MODE OF CARRYING OUT THE INVENTION

The following describes the present invention further in detail with reference to formulation and Examples. It goes without saying that the present invention is not restricted by these examples.

Formulation Example (Tablets)

| Composition | 20 mg Tablets |
|---|---|
| Compound of the present invention | 20 mg |
| Lactose | 75 |
| Corn starch | 16 |
| Hydroxypropylcellulose | 4.5 |
| Carboxymethylcellulose calcium | 8.8 |
| Magnesium stearate | 0.7 |
| Total | 120 mg |

20 mg Tablets

Using a fluidized granulation coating apparatus, 100 g of a compound of the present invention was uniformly mixed with 375 g of lactose and 80 g of corn starch. This was made into granules by spraying 10% hydroxypropylcellulose solution. After drying, the resulting granules were passed through a 20 mesh screen, 19 g of carboxymethylcellulose calcium and 3.5 g of magnesium stearate were added, and the mixture was made into tablets of 120 mg per tablet by a rotary tablet making machine using a die-punch system of 7 mm×8.4 R.

EXAMPLE 1

1-[5-(3-Benzyl-1,2,4-oxadiazol-5-yl)-2-thenyl]hexahydro-1H-azepine hydrochloride 535 mg (2.0 mmol) of ethyl 5-[(hexahydro-1H-azepin-1-yl)methyl-2-thienyl]carboxylate and 360 mg (2.4 mmol) of 2-phenylacetoamidoxime were dissolved in 20 ml of tetrahydrofuran, 120 mg (3.0 mmol) of sodium hydride was added at room temperature, and then the mixture was heated under reflux for 2 hours. The resulting insoluble matter was removed by filtration, and the resulting filtrate was concentrated under a reduced pressure. To the resulting residue was added water, and the mixture was extracted with ethyl acetate. The resulting organic layer was washed with saturated brine and then dried over anhydrous magnesium sulfate. The solvent was evaporated under a reduced pressure, and the resulting residue was subjected to a silica gel column chromatography, which was eluted with chloroform-methanol (80:1) to give 343 mg of the title compound in its free form. 960 mg (2.72 mmol) of the free form compound was dissolved in 30 ml of ethyl acetate, 0.7 ml (2.8 mmol) of 4 N HCl/AcOEt was added dropwise, and the thus precipitated crystals were collected by filtration and recrystallized from acetonitrile to give 690 mg of the title compound.

Melting point: 189–192° C.

¹H-NMR (δ ppm in DMSO-$d_6$) 1.53–1.59 (2H, m), 1.65–1.67 (2H, m), 1.82–1.85 (4H, m), 3.02–3.08 (2H, m), 3.41 (1H, br), 4.15 (2H, s), 4.64 (2H, d, J=5.5 Hz), 7.27 (1H, m), 7.34 (4H, br), 7.63 (1H, d, J=3.7 Hz), 7.97 (1H, d, J=3.7 Hz), 11.36 (1H, br)

EXAMPLE 2

1-[5-(3-Phenetyl-1,2,4-oxadiazol-5-yl)-2-thenyl] hexahydro-1H-azepine hydrochloride In the same manner as described in Example 1, 650 mg of the title compound was obtained from 1.34 g (5.0 mmol) of ethyl 5-[(hexahydro-1H-azepin-1-yl)methyl-2-thienyl] carboxylate and 985 mg (6.0 mmol) of 3-phenylpropionamidoxime.

Melting point: 180–182° C.

¹H-NMR (δ ppm in DMSO-$d_6$) 1.56–1.60 (2H, m), 1.66–1.68 (2H, m), 1.84 (4H, br), 3.03–3.09 (6H, m), 4.66 (2H, d, J=4.9 Hz), 7.21 (1H, m), 7.26–7.30 (4H, m), 7.64 (1H, d, J=3.7 Hz), 7.98 (1H, d, J=3.7 Hz), 11.24 (1H, br)

EXAMPLE 3

1-[5-[3-(3-Phenylpropyl)-1,2,4-oxadiazol-5-yl]-2-thenyl] hexahydro-1H-azepine hydrochloride In the same manner as described in Example 1, 560 mg of the title compound was obtained from 1.34 g (5.0 mmol) of ethyl 5-[(hexahydro-1H-azepin-1-yl)methyl-2-thienyl] carboxylate and 1.07 g (6.0 mmol) of 4-phenylbutylamidoxime.

Melting point: 174–176° C. (acetonitrile)

¹H-NMR (δ ppm in DMSO-$d_6$) 1.55–1.60 (2H, m), 1.64–1.67 (2H, m), 1.83 (4H, br), 1.98–2.04 (2H, m), 2.66–2.69 (2H, m), 2.74–2.77 (2H, m), 3.05–3.09 (2H, m), 4.66 (2H, d, J 5.5 Hz), 7.18–7.31 (5H, m), 7.62 (1H, d, J 3.7 Hz), 7.98 (1H, d, J=3.7 Hz), 11.07 (1H, br)

EXAMPLE 4

1) 5-[5-[(Hexahydro-1H-azepin-1-yl)methyl]-2-thienyl]-3-tetrahydropyranyloxymethyl-1,2,4-oxadiazole In the same manner as described in Example 1, 4.4 g of the title compound was obtained from 8.0 g (29.9 mmol) of ethyl 5-[(hexahydro-1H-azepin-1-yl)methyl-2-thienylicarboxylate and 6.3g (35.9 mmol) of 2-(tetrahydropyranyloxy)acetoamidoxime.

1H-NMR (δ ppm in CDCl₃) 1.55–1.90 (10H, m), 2.60–2.70 (4H, m), 3.30–3.73 (3H, m), 3.85–4.23 (4H, m), 4.70 (1H, d, J=13.4 Hz), 4.80–4.96 (3H, m), 6.95 (1H, d, J=3.7 Hz), 7.75 (1H, d, J=3.7 Hz) 2) 5-[5-((Hexahydro-1H-azepin-1-yl)methyl]-2-thienyl]-1,2,4-oxadiazole-3-methanol 75 ml (75 mmol) of 1 N HCl was added dropwise to 80 ml ethanol solution of 6.23 g (16.74 mmol) of the compound obtained in the above step 1), and the mixture was stirred at room temperature for 4 hours. The reaction mixture was concentrated under a reduced pressure, 80 ml of 1 N NaOH was added to the residue, and the mixture was extracted with ethyl acetate. Then, the resulting organic layer was washed with saturated brine. The organic layer was dried over anhydrous magnesium sulfate, the solvent was evaporated under a reduced pressure, and the resulting residue was subjected to a silica gel column chromatography, which was eluted with chloroform-methanol (75:1) to give 3.76 g of the title compound.

Melting point: 79–81° C. (isopropyl ether)

¹H-NMR (δ ppm in CDCl₃) 1.58–1.78 (9H, m), 2.68–2.70 (4H, m), 3.88 (2H, m), 3.88 (2H, s), 4.83 (2H, s), 6.96 (1H, d, J=3.7 Hz), 7.75 (1H, d, J=3.7 Hz)

EXAMPLE 5

1-[5-(3-Benzyloxymethyl-1,2,4-oxadiazol-5-yl)-2-thenyl]hexahydro-1H-azepine hydrochloride In an atmosphere of argon and at 0° C., 20 ml of tetrahydrofuran solution containing 820 mg (2.8 mmol) of the compound obtained in Example 4-2) was added dropwise to 10 ml tetrahydrofuran suspension of 118 mg (2.94 mmol) of sodium hydride, and the mixture was stirred for 15 minutes. Then, 0.35 ml (2.94 mmol) of benzyl bromide and 10 mg of tetrabutylammonium iodide were added, followed by stirring at room temperature for 16 hours. To the reaction solution was added water, and the mixture was extracted with ethyl acetate. The resulting organic layer was washed with saturated brine and dried over anhydrous magnesium sulfate. The solvent was evaporated under a reduced pressure and the resulting residue was subjected to a silica gel column chromatography, which was eluted with chloroform-methanol (80:1) to give 580 mg of the title compound in its free form. Then, 0.3 ml of 4 N HCl/AcOEt was added, and the thus precipitated crystals were collected by filtration and recrystallized from acetonitrile-ethyl acetate to give 467 mg of the title compound.

Melting point: 166–168° C.

¹H-NMR (δ ppm in DMSO-$d_6$) 1.55–1.60 (2H, m), 1.65–1.67 (2H, m), 1.84 (4H, br), 3.04–3.12 (2H, m), 4.63 (2H, s), 4.67–4.69 (2H, m), 4.71 (2H, s), 7.33 (1H, m), 7.37 (5H, m), 7.65 (1H, d, J =3.7 Hz), 8.03 (1H, d, J=3.7 Hz), 11.21 (1H, br)

EXAMPLE 6

[5-[5-[(Hexahydro-1H-azepin-1-yl)methyl]-2-thienyl]-1,2,4-oxadiazol-3-yllmethyl benzoate 1.0 oxalate 450 mg (1.53 mmol) of the compound obtained in the step 2) of Example 4 was dissolved in 30 ml of methylene chloride, 0.32 ml (2.3 mmol) of triethylamine and 0.21 ml (1.84 mmol) of benzoyl chloride were added, and the mixture was stirred overnight at room temperature. The reaction solution was washed with water, and the organic layer was dried over anhydrous magnesium sulfate. The solvent was evaporated under a reduced pressure and the resulting residue was subjected to a silica gel column chromatography, which was eluted with chloroform-methanol (75:1) to give 550 mg of the title compound in its free form. A 180 mg (0.453 mmol) portion of this compound was dissolved in 5 ml of methanol, 5 ml of methanol solution containing 40 mg (0.44 mmol) of oxalic acid was added, and the mixture was stirred at room temperature for 10 minutes. The solvent was evaporated under a reduced pressure and then small amounts of methanol and ether were added to the resulting residue to effect its crystallization. By collecting the thus formed crystals by filtration and drying them, 166 mg of the title compound was obtained.

Melting point: 120–121° C.

¹H-NMR (δ ppm in DMSO-$d_6$) 8.03–8.01 (2H, m), 7.97 (1H, d, J=3.7 Hz), 7.72 (1H, m), 7.59–7.56 (2H, m), 7.34 (1H, d, J=3.7 Hz), 5.56 (2H, s), 4.28 (2H, s), 2.93 (4H, brs), 1.70 (4H, brs), 1.59 (4H, brs)

EXAMPLE 7

[5-[5-[(Hexahydro-1H-azepin-1-yl)methyl]-2-thienyl]-1,2,4-oxadiazol-3-yl]methyl N-benzylcarbamate 1.0 oxalate 480 mg (1.64 mmol) of the compound obtained in the step 2) of Example 4 was dissolved in 10 ml of N,N-dimethylformamide to which was subsequently added dropwise 5 ml of N,N-dimethylformamide suspension containing 162 mg (1.64 mmol) of copper (I) chloride and 229 mg (1.72 mmol) of benzyl isocyanate, and the resulting mixture was stirred overnight at room temperature. The reaction solution was concentrated under a reduced pressure, and the resulting residue was dissolved in chloroform, washed with water and then dried over anhydrous magnesium sulfate. The solvent was evaporated under a reduced pressure and the resulting residue was subjected to a silica gel column chromatography to give 690 mg of the title compound in its free form. A 520 mg portion of this compound was subjected to salt formation in the same manner described in Example 6 using 104 mg of oxalic acid to give 398 mg of the title compound.

Melting point: 129–130° C.

$^1$H-NMR ($\delta$ ppm in DMSO-$d_6$) 8.05 (1H, t), 7.94 (1H, d), 7.32–7.22 (6H, m), 5.23 (2H, s), 4.26–4.22 (4H, m), 2.92 (4H, br), 1.70 (4H, brs), 1.59 (4H, brs)

EXAMPLE 8

1-[5-(3-Aminomethyl-1,2,4-oxadiazol-5-yl)-2-thienyl] hexahydro-1H-azepine dihydrochloride With ice-cooling, 1.1 g (7.5 mmol) of phthalimide, 1.97 g (7.5 mmol) of triphenylphosphine and 1.31 g (7.5 mmol) of diethyl azodicarboxylate were added to 50 ml of tetrahydrofuran solution containing 2.0 g (6.82 mmol) of the compound obtained in the step 2) of Example 4 , and the mixture was stirred at room temperature for 2 hours. The reaction solution was concentrated under a reduced pressure, and the resulting residue was dissolved in 50 ml of ethanol. Then, 3.3 ml (68.2 mmol) of hydrazine hydrate was added dropwise, and then the resulting mixture was stirred at room temperature for 2 hours. The reaction solution was concentrated under a reduced pressure, and the resulting residue was acidified by adding 1 N HCl and then washed with chloroform. Next, the resulting water layer was alkalified by adding 4 N sodium hydroxide aqueous solution and then extracted with ethyl acetate. The resulting organic layer was washed with saturated brine and then dried over anhydrous magnesium sulfate. The solvent was evaporated under a reduced pressure and the resulting residue was subjected to a silica gel column chromatography, which was eluted with chloroform-methanol (30:1) to give 1.86 g of the title compound in its free form. 400 mg of this compound was subjected to salt formation using 1N HCl and then recrystallized from isopropanol to give 362 mg of the title compound.

Melting point: 230–232° C.

$^1$H-NMR ($\delta$ ppm in DMSO-$d_6$) 1.59–1.66 (4H, m), 1.85 (4H, m), 3.08 (2H, br), 4.31 (2H, s), 4.67 (2H, s), 7.68 (1H, d, J=3.7 Hz), 8.05 (1H, d, J=3.7 Hz), 8.92 (3H, br), 11.79 (1H, br)

EXAMPLE 9

1-Benzyl-3-[[5-[5-[(hexahydro-1H-azepin-1-yl)methyl]-2-thienyl]-1,2,4-oxadiazol-3-yl]methyl]urea 770 mg (2.63 mmol) of the free form compound obtained in Example 8 was dissolved in 20 ml of DMF, and 5 ml of DMF solution containing 369 mg (2.77 mmol) of benzyl isocyanate was added, and the mixture was stirred at room temperature for 1 hour. The reaction solution was concentrated under a reduced pressure, and the resulting residue was dissolved in chloroform, washed with water and then dried over anhydrous magnesium sulfate. The solvent was evaporated and the resulting residue was subjected to a silica gel column chromatography, which was eluted with chloroform-methanol (50:1) to give 1.0 g of the title compound.

Melting point: 101–103° C.

$^1$H-NMR ($\delta$ ppm in CDCl$_3$) 7.70 (1H, d, J=3.7 Hz), 7.31–7.26 (5H, m), 6.95 (1H, d, J=3.7 Hz), 5.10 (2H, m), 4.57 (2H, d, J=5.7 Hz), 4.42 (2H, d, J=5.7 Hz), 3.88 (2H, s), 2.71 (4H, m), 1.64 (8H, brs)

EXAMPLE 10

N-[[5-[5-[(Hexahydro-1H-azepin-1-yl)methyl]-2-thienyl]-1,2,4-oxadiazol-3-yl]methyl]benzamide 1.0 fumarate 585 mg (2.0 mmol) of the free form compound obtained in Example 8 was dissolved in 20 ml of methylene chloride, 0.6 ml (4.0 mmol) of triethylamine, 0.28 ml (2.4 mmol) of benzoyl chloride and 4-DMAP (cat.) were added, and the mixture was stirred at room temperature for 19 hours. The reaction solution was washed with water and then dried over anhydrous magnesium sulfate. The solvent was evaporated, and the resulting residue was subjected to a silica gel column chromatography, which was eluted with chloroform-methanol (80:1) to give 510 mg of the title compound in its free form. Using 140 mg (1.2 mmol) of fumaric acid, a 490 mg (1.24 mmol) portion of this compound was subjected to salt formation to give 348 mg of the title compound.

Melting point: 79–81° C.

$^1$H-NMR ($\delta$ ppm in DMSO-$d_6$) 9.22 (1H, t), 7.91–7.85 (3H, m), 7.58–7.48 (3H, m), 7.16 (1H, d), 6.92 (2H, s), 4.62 (2H, d), 3.91 (2H, s), 2.67–2.64 (4H, m), 1.57 (8H, brs)

EXAMPLE 11 a) N-Benzyl-5-[5-[(hexahydro-1H-azepin-1-yl)methyl]-2-thienyl]-1,2,4-oxadiazol-3-ylmethylamine dihydrochloride b) N,N-Dibenzyl-5-[5-[(hexahydro-1H-azepin-1-yl)methyl]-2-thienyl]-1,2,4-oxadiazol-3-ylmethylamine dihydrochloride 0.53 ml (5.2 mmol) of benzaldehyde was added dropwise to 55 ml of 1,2-dichloroethane solution containing 1.52 g of the free form compound obtained in Example 8, the mixture was stirred at room temperature for 2.5 hours, 1.44 g (6.76 mmol) of NaBH(OAc) and 0.6 ml of acetic acid were added dropwise thereto, and then the resulting mixture was further stirred at room temperature for 2 days. To the reaction solution was added concentrated aqueous ammonia, and the organic layer was separated and dried over anhydrous magnesium sulfate. The solvent was evaporated, and the resulting residue was subjected to a silica gel column chromatography, which was eluted with chloroform-methanol (100:1→80:1) to give 359 mg of the free form of b) and 980 mg of the free form of a). They were subjected to salt formation using 4 N HCl/AcOEt, thereby obtaining the title compounds b) in 330 mg and a) in 1,036 mg.

a) $^1$H-NMR ($\delta$ ppm in DMSO-$d_6$) 11.84 (1H, br), 10.42 (2H, br), 8.06 (1H, d), 7.70 (1H, d), 7.61–7.59 (2H, m), 7.45–7.25 (3H, m), 4.68 (2H, brs), 4.42 (2H, brs), 4.30 (2H, brs), 3.33 (2H, br), 3.08 (2H, br), 1.99–1.89 (4H, m), 1.67 (4H, br), 1.58 (4H, br) MS (FAB, Pos, m/z) 383 (M$^+$+1)

b) $^1$H-NMR ($\delta$ ppm in DMSO-$d_6$) 11 64 (1H, br), 8.04 (1H, d), 7.70 (1H, d), 7.55 (4H, br), 7.43–7.39 (6H, m), 4.68 (2H, d), 4.11 (4H, br), 3.33 (2H, m), 3.11–3.05 (2H, m), 1.91–1.85 (4H, m), 1.69–1.65 (4H, m), 1.61–1.55 (4H, m) MS (FAB, Pos, m/z) 473 (M$^+$+1)

EXAMPLE 12

1) 3-tert-Butyldimethylsiloxyethyl-5-[5-[(hexahydro-1H-azepin-1-yl)methyl]-2-thienyl]-1,2,4-oxadiazole Using 12.0 g (44.9 mmol) of ethyl 5-[(hexahydro-1H-azepin-1-yl)methyl]-2-thienyl]carboxylate and 12.7 g (58.3 mmol) of 3-tert-butyldimethylsiloxypropioamidoxime, 9.62 g of the title compound was obtained in the same manner as described in Example 1.

$^1$H-NMR (δ ppm in CDCl$_3$) 0.04 (6H, s), 0.86 (9H, s), 1.63–1.70 (8H, m), 2.69 (4H, m), 2.99 (2H, t, J=6.8 Hz), 3.87 (2H, s), 4.04 (2H, t, J=6.8 Hz), 6.94 (1H, d, J=3.9 Hz), 7.71 (1H, d, J=3.9 Hz)

2) 5-[5-[ (Hexahydro-1H-azepin-1-yl)methyl]-2-thienyl]-1,2,4-oxadiazole-3-ethanol hydrochloride With ice-cooling, 28.4 ml (28.4 mmol) of tetrabutylammonium fluoride (1.0 M solution in THF) was added dropwise to 250 ml of tetrahydrofuran solution containing 9.97 g (25.2 mmol) of the compound obtained in the above step 1), and the mixture was stirred for 1 hour at the same temperature. The reaction solution was concentrated and the resulting residue was acidified by adding 1 N HCl and then washed with chloroform. The resulting water layer was alkalified by adding 4 N NaOH and extracted with ethyl acetate, the resulting organic layer was washed with saturated brine and dried over anhydrous magnesium sulfate. Then, the solvent was evaporated to give 7.27 g (quant.) of the title compound in its free form. A 950 mg (3.09 mmol) portion of this compound was converted into its salt using 4 N HCl/AcOEt and then recrystallized from acetonitrile to give 639 mg of the title compound.

Melting point: 229–231° C.

$^1$H-NMR (δ ppm in DMSO-d$_6$) 1.50–1.78 (4H, m), 1.83 (4H, br), 2.87–2.90 (2H, m), 3.05–3.09 (2H, m), 3.78–3.80 (2H, m), 4.66–4.68 (2H, m), 7.62 (1H, d, J=3.7 Hz), 7.98 (1H, d, J=3.7 Hz), 11.06 (1H, br)

EXAMPLE 13

1-[5-[3-(2-Benzyloxyethyl)-1,2,4-oxadiazol-5-yl]-2-thenyl]hexahydro-1H-azepine hydrochloride In the same manner as described in Example 1, 850 mg of the title compound was obtained in its free form from 1.34 g (5.0 mmol) of ethyl 5-[(hexahydro-1H-azepin-1-yl)methyl]-2-thienyl]carboxylate and 1.8 g (9.28 mmol) of 3-benzyloxypropionamidoxime. This was converted into its salt using 4 N HCl/AcOEt and then recrystallized from acetonitrile to give 440 mg of the title compound.

Melting point: 145–147° C.

$^1$H-NMR (δ ppm in DMSO-d$_6$) 1.50–1.75 (4H, m), 1.84 (4H, m), 3.04–3.10 (4H, m), 3.82–3.85 (2H, m), 4.51 (2H, s), 4.66–4.68 (2H, m), 7.20–7.38 (5H, m), 7.64 (1H, d, J=3.7 Hz), 7.98 (1H, d, J=3.7 Hz), 11.28 (1H, br)

EXAMPLE 14

1-[5-[3-(2-Ethoxyethyl)-1,2,4-oxadiazol-5-yl]-2-thenyl]hexahydro-1H-azepine hydrochloride In the same manner as described in Example 1, 507 mg of the title compound was obtained from 1.07 g (4.0 mmol) of ethyl 5-[(hexahydro-1H-azepin-1-yl)methyl]-2-thienyl]carboxylate and 0.8 g (6.0 mmol) of 3-ethoxypropylamidoxime.

Melting point: 149–151° C.

$^1$H-NMR (δ ppm in DMSO-d$_6$) 11.10 (1H, br), 7.99 (1H, d), 7.63 (1H, d), 4.67 (2H, S), 3.77 (2H, t), 3.47–3.43 (2H, m), 3.38–3.35 (4H, m), 2.99 (2H, t), 1.84 (4H, m), 1.67–1.64 (2H, m), 1.60–1.55 (2H, m), 1.08 (3H, t)

EXAMPLE 15

1-[5-(3-Vinyl-1,2,4-oxadiazol-5-yl)-2-thenyl]hexahydro-1H-azepine hydrochloride

To 25 ml of tetrahydrofuran solution containing 615 mg (2.0 mmol) of the free form compound obtained in the step 2) of Example 12 was added 418 mg (3.0 mmol) of 4-nitrophenol, 786 mg (3.0 mmol) of triphenylphosphine and 0.48 ml (3.0 mmol) of diethyl azodicarboxylate, and the mixture was stirred overnight at room temperature. The reaction solution was concentrated, and the resulting residue was subjected to a silica gel column chromatography to give 260 mg of the title compound in its free form. This was converted into its salt using 4 N HCl/AcOEt to give 191 mg of the title compound.

Melting point: 173–174° C.

$^1$H-NMR (δ ppm in DMSO-d$_6$) 11 07 (1H, br), 8.03 (1H, d, J=3.7 Hz), 7.64 (1H, d, J=3.7 Hz), 6.85 (1H, m), 6.40 (1H, m), 5.94 (1H, m), 4.68 (2H, s), 3.39–3.34 (4H, br), 1.84 (4H, br), 1.67–1.64 (2H, m), 1.61–1.57 (2H, m)

EXAMPLE 16

2-[5-[5-[(Hexahydro-1H-azepin-1-yl)methyl]-2-thienyl]-1,2,4-oxadiazol-3-yl]ethyl benzoate 1.0 oxalate In the same manner as described in Example 6, 580 mg of the title compound was obtained in its free form from 450 mg (1.46 mmol) of the free form compound obtained in the step 2) of Example 12. A 541 mg (1.31 mmol) portion of this was converted into its salt using 112.5 mg (1.25 mmol) of oxalic acid to give 384 mg of the title compound.

Melting point: 121–123° C.

$^1$H-NMR (δ ppm in DMSO-d$_6$) 7.96–7.90 (3H, m), 7.60 (1H, m), 7.52 (2H, t, J=7.9 Hz), 7.32 (1H, br), 4.65 (2H, t, J=6.1 Hz), 4.25 (2H, br), 3.26 (2H, t, J=6.1 Hz), 2.92 (4H, brs), 1.69 (4H, brs), 1.59 (4H, brs)

EXAMPLE 17

2-[5-[5-[(Hexahydro-1H-azepin-1-yl)methyl]-2-thienyl]-1,2,4-oxadiazol-3-yl]ethyl 4-methoxybenzoate oxalate In the same manner as described in Example 6, 444 mg of the title compound was obtained from 307 mg (1.0 mmol) of the free form compound obtained in the step 2) of Example 12 and 205 mg (1.2 mmol) of 4-methoxybenzoyl chloride.

Melting point: 131–132° C.

$^1$H-NMR (δ ppm in DMSO-d$_6$) 7.91 (1H, d), 7.88–7.86 (2H, m), 7.31 (1H, d), 7.04–7.02 (2H, m), 4.60 (2H, t), 4.25 (2H, br), 3.82 (3H, s), 3.24 (2H, t), 2.92 (4H, br), 1.69 (4H, br), 1.59 (4H, br)

EXAMPLE 18

2-[5-[5-[(Hexahydro-1H-azepin-1-yl)methyl]-2-thienyl]-1,2,4-oxadiazol-3-yl]ethyl 4-fluorobenzoate oxalate In the same manner as described in Example 6, 438 mg of the title compound was obtained from 307 mg (1.0 mmol) of the free form compound obtained in the step 2) of Example 12 and 0.14 ml (1.2 mmol) of 4-fluorobenzoyl chloride.

Melting point: 96–97° C. $^1$H-NMR (δ ppm in DMSO-d$_6$) 8.01–7.98 (2H, m), 7.91 (1H, d), 7.38–7.33 (3H, m), 4.64 (2H, t), 4.28 (2H, br), 3.26 (2H, t), 2.94 (4H, br), 1.70 (4H, br), 1.59 (4H, br)

EXAMPLE 19

2-[5-[5-[(Hexahydro-1H-azepin-1-yl)methyl]-2-thienyl]-1,2,4-oxadiazol-3-yl]ethyl 4-nitrobenzoate In the same manner as described in Example 6, 439 mg of the title compound was obtained from 307 mg (1.0 mmol) of the free form compound obtained in the step 2) of Example 12 and 4-nitrobenzoyl chloride.

Melting point: 67–69° C.

$^1$H-NMR (δ ppm in CDCl$_3$) 8.40–8.10 (4H, m), 7.72 (1H, d, J=3.7 Hz), 6.96 (1H, d, J=3.7 Hz), 4.79 (2H, t, J=6.4 Hz), 3.80 (2H, s), 3.27 (2H, t, J=6.4 Hz), 2.70 (4H, br), 1.64 (8H, br)

EXAMPLE 20

2-[5-[5-[(Hexahydro-1H-azepin-1-yl)methyl]-2-thienyl]-1,2,4-oxadiazol-3-yl]ethyl cyclohexanecarboxylate In the same manner as described in Example 6, 409 mg of the title compound was obtained from 307 mg (1.0 mmol) of the free form compound obtained in the step 2) of Example 12 and 0.16 ml (1.2 mmol) of cyclohexanecarbonyl chloride.

Melting point: 41–42° C.

$^1$H-NMR (δ ppm in CDCl$_3$) 7.72 (1H, d), 6.95 (1H, d), 4.48 (2H, t), 3.88 (2H, s), 3.10 (2H, t), 2.69 (2H, t), 2.70–2.68 (4H, m), 2.29 (1H, m), 1.90–1.86 (2H, m), 1.75–1.61 (1OH, m), 1.47–1.37 (2H, m), 1.31–1.16 (4H, m)

EXAMPLE 21

2-[5-[5-[(Hexahydro-1H-azepin-1-yl)methyl]-2-thienyl]-1,2,4-oxadiazol-3-yl]ethyl acetate 1.0 fumarate In the same manner as described in Example 6, 330 mg of the title compound was obtained from 615 mg (2.0 mmol) of the free form compound obtained in the step 2) of Example 12 and 0.38 ml (4.0 mmol) of acetic anhydride.

Melting point: 105–106° C.

$^1$H-NMR (δ ppm in DMSO-d$_6$) 7.85 (1H, d, J=3.7 Hz), 7.16 (1H, d, J=3.7 Hz), 6.62 (2H, s), 4.38 (2H, t, J=6.1 Hz), 3.93 (2H, s), 3.09 (2H, t, J=6.1 Hz), 3.69–3.67 (4H, m), 1.99 (3H, s), 1.61–1.59 (8H, m)

EXAMPLE 22

1-[5-[(3-Methyl-1,2,4-oxadiazol-5-yl)-2-thenyl] hexahydro-1H-azepine

In the same manner as described in Example 1, 280 mg of the title compound was obtained from 570 mg (7.70 mmol) of acetamidooxime and 1.03 g (3.85 mmol) of ethyl 5-[(hexahydro-1H-azepin-1-yl)methyl-2-thienyl] carboxylate.

Melting point: 45–46° C.

$^1$H-NMR (δ ppm in CDCl$_3$) 7.71 (1H, d), 6.95 (1H, d), 3.88 (2H, s), 2.70–2.64 (4H, m), 2.43 (3H, s), 1.64 (8H brs)

EXAMPLE 23

2-[5-[5-[(Hexahydro-1H-azepin-1-yl)methyl]-2-thienyl]-1,2,4-oxadiazol-3-yl]ethyl N-benzylcarbamate 1.0 fumarate In the same manner as described in Example 7, 570 mg of the title compound was obtained in its free form from 610 mg (1.98 mmol) of the free form compound obtained in the step 2) of Example 12 and 278 mg (2.08 mmol) of benzyl isocyanate. A 560 mg portion of this was converted into its salt using 141 mg of fumaric acid to give 366 mg of the title compound.

Melting point: 138–139° C.

$^1$H-NMR (δ ppm in DMSO-d$_6$) 7.84 (1H, d, J=3.7 Hz), 7.72 (1H, t), 7.30–7.16 (5H, m), 6.62 (2H, s), 4.36 (2H, t, J=6.1 Hz), 4.15 (2H, d, J=6.1 Hz), 3.93 (2H, s), 3.07 (2H, t, J=6.1 Hz), 2.68–2.66 (4H, m), 1.61–1.58 (8H, m)

EXAMPLE 24

2-[5-[5-[(Hexahydro-1H-azepin-1-yl)methyl]-2-thienyl]-1,2,4-oxadiazol-3-yl]ethyl N-ethylcarbamate 1.0 oxalate In the same manner as described in Example 7, 198 mg of the title compound was obtained from 330 mg (1.07 mmol) of the free form compound obtained in the step 2) of Example 12 and 82 mg (1.15 mmol) of ethyl isocyanate.

Melting point: 112–113° C.

$^1$H-NMR (δ ppm in DMSO-d$_6$) 7.92 (1H, d), 7.33 (1H, d), 7.12 (1H, br), 4.31 (2H, t), 4.27 (2H, br), 3.05 (2H, t), 3.00–2.93 (6H, m), 1.70 (4H, br), 1.59 (4H, br), 0.98 (3H, t)

EXAMPLE 25

2-[5-[5-[(Hexahydro-1H-azepin-1-yl)methyl]-2-thienyl]-1,2,4-oxadiazol-3-yl]ethyl N-(2-chloroethyl)carbamate 1.0 oxalate In the same manner as described in Example 7, 437 mg of the title compound was obtained from 462 mg (1.5 mmol) of the free form compound obtained in the step 2) of Example 12 and 0.15 ml (1.65 mmol) of 2-chloroethyl isocyanate.

Melting point: 71–72° C.

$^1$H-NMR (δ ppm in DMSO-d$_6$) 7.92 (1H, d), 7.45 (1H, t), 7.34 (1H, d), 4.35 (2H, t), 4.29 (2H, br), 3.56 (2H, t), 3.29–3.24 (2H, m), 3.07 (2H, t), 2.94 (4H, br), 1.71 (4H, br), 1.59 (4H, br)

EXAMPLE 26

2-[5-[5-[(Hexahydro-1H-azepin-1-yl)methyl]-2-thienyl]-1,2,4-oxadiazol-3-yl]ethyl N-butylcarbamate 1.0 oxalate In the same manner as described in Example 7, 573 mg of the title compound was obtained from 462 mg (1.5 mmol) of the free form compound obtained in the step 2) of Example 12 and 0.19 ml (1.65 mmol) of n-butyl isocyanate.

Melting point: 109–110° C.

$^1$H-NMR (δ ppm in DMSO-d$_6$) 7.93 (1H, d), 7.37 (1H, d), 7.13 (1H, t), 4.34–4.30 (4H, m), 3.06 (2H, t), 2.99 (4H, m), 2.94–2.91 (2H, m), 1.72 (4H, br), 1.59 (4H, br), 1.36–1.30 (2H, m), 1.26–1.20 (2H, m), 0.86 (3H, t)

EXAMPLE 27

2-[5-[5-[(Hexahydro-1H-azepin-1-yl)methyl]-2-thienyl]-1,2,4-oxadiazol-3-yl]ethyl N-tert-butylcarbamate 1.0 oxalate In the same manner as described in Example 7, 378 mg of the title compound was obtained from 462 mg (1.5 mmol) of the free form compound obtained in the step 2) of Example 12 and 0.19 ml (1.65 mmol) of t-butyl isocyanate.

Melting point: 140–141° C.

$^1$H-NMR (δ ppm in DMSO-d$_6$) 7.92 (1H, d), 7.34 (1H, d), 6.90 (1H, br), 4.29–4.27 (4H, m), 3.04 (2H, t), 2.95 (4H, br), 1.71 (4H, br), 1.59 (4H, br), 1.18 (9H, s)

EXAMPLE 28

2-[5-[5-[(Hexahydro-1H-azepin-1-yl)methyl]-2-thienyl]-1,2,4-oxadiazol-3-yl]ethyl N-cyclohexylcarbamate 1.0 oxalate In the same manner as described in Example 7, 363 mg of the title compound was obtained from 462 mg (1.5 mmol) of the free form compound obtained in the step 2) of Example 12 and 0.25 ml (1.95 mmol) of cyclohexyl isocyanate.

Melting point: 78–79° C.

$^1$H-NMR (δ ppm in DMSO-d$_6$) 7.92 (1H, d), 7.35 (1H, d), 7.08 (1H, d), 4.31 (2H, t), 3.38 (1H, m), 3.21 (1H, br), 3.05 (2H, t), 2.96 (4H, br), 1.71 (6H, br), 1.59 (6H, br), 1.22–1.06 (6H, m)

EXAMPLE 29

2-[5-[5-[(Hexahydro-1H-azepin-1-yl)methyl]-2-thienyl]-1,2,4-oxadiazol-3-yl]ethyl N-phenylcarbamate In the same manner as described in Example 7, 515 mg of the title compound was obtained from 462 mg (1.5 mmol) of the free form compound obtained in the step 2) of Example 12 and 232 mg (1.95 mmol) of phenyl isocyanate.

Melting point: 68–70° C.

$^1$H-NMR (δ ppm in DMSO-$d_6$) 7.73 (1H, d), 7.37–7.27 (3H, m), 7.05 (1H, m), 6.96 (1H, d), 6.66 (1H, br), 4.60 (2H, t), 3.88 (2H, br), 3.16 (2H, t), 2.70–2.68 (4H, m), 1.65 (8H, m)

EXAMPLE 30

2-[5-[5-[(Hexahydro-1H-azepin-1-yl)methyl]-2-thienyl]-1,2,4-oxadiazol-3-yl]ethyl N-(4-nitrophenyl)carbamate In the same manner as described in Example 7, 604 mg of the title compound was obtained from 462 mg (1.5 mmol) of the free form compound obtained in the step 2) of Example 12 and 320 mg (1.95 mmol) of 4-nitrophenyl isocyanate.

Melting point: 73–74° C.

$^1$H-NMR (δ ppm in DMSO-$d_6$) 8.29–8.26 (2H, m), 8.22–8.19 (2H, m), 7.54 (1H, m), 6.96 (1H, d), 4.79 (2H, t), 3.88 (2H, br), 3.28 (2H, t), 2.70–2.68 (4H, m), 1.66–1.63 (8H, m)

EXAMPLE 31

2-[5-[5-[(Hexahydro-1H-azepin-1-yl)methyl]-2-thienyl]-1,2,4-oxadiazol-3-yl]ethyl N-(4-methoxyphenyl)carbamate 1.0 oxalate In the same manner as described in Example 7, 652 mg of the title compound was obtained from 462 mg (1.5 mmol) of the free form compound obtained in the step 2) of Example 12 and 291 mg (1.95 mmol) of 4-methoxyphenyl isocyanate.

Melting point: 83–84° C.

$^1$H-NMR (δ ppm in DMSO-$d_6$) 9.45 (1H, br), 7.93 (1H, d), 7.36–7.33 (3H, m), 6.86–6.82 (2H, m), 4.45 (2H, t), 4.27 (2H, br), 3.69 (3H, s), 3.15 (2H, t), 2.93 (4H, br), 1.70 (4H, br), 1.59 (4H, br)

EXAMPLE 32

2-[5-[5-[(Hexahydro-1H-azepin-1-yl)methyl]—2-thienyl]-1,2,4-oxadiazol-3-yl]ethyl N-(4-fluorophenyl) carbamate 1.0 oxalate In the same manner as described in Example 7, 465 mg of the title compound was obtained from 462 mg (1.5 mmol) of the free form compound obtained in the step 2) of Example 12 and 267 mg (1.95 mmol) of 4-fluorophenyl isocyanate.

Melting point: 93–94° C.

$^1$H-NMR (δ ppm in DMSO-$d_6$) 9.70 (1H, br), 7.93 (1H, d), 7.46–7.42 (2H, m), 7.34 (1H, d), 7.10 (2H, t), 4.47 (2H, t), 4.30 (2H, br), 3.16 (2H, t), 2.96–2.94 (4H, m), 1.70 (4H, br), 1.59 (4H, br)

EXAMPLE 33

2-(5-[5-[(Hexahydro-1H-azepin-1-yl)methyl]-2-thienyl]-1,2,4-oxadiazol-3-yl]ethyl N-(2-nitrophenyl)carbamate 1.0 oxalate In the same manner as described in Example 7, 440 mg of the title compound was obtained from 462 mg (1.5 mmol) of the free form compound obtained in the step 2) of Example 12 and 271 mg (1.65 mmol) of 2-nitrophenyl isocyanate.

Melting point: 88–89° C.

$^1$H-NMR (δ ppm in DMSO-$d_6$) 9.87 (1H, br), 7.96–7.93 (2H, m), 7.69–7.61 (2H, m), 7.35–7.30 (2H, m), 4.47 (2H, t), 4.31 (2H, br), 2.96 (2H, br), 1.71 (4H, br), 1.59 (1H, br)

EXAMPLE 34

N-[2-[5-[5-[(Hexahydro-1H-azepin-1-yl)methyl]-2-thienyl]-1,2,4-oxadiazol-3-yl]ethyl]phthalimide hydrochloride To 100 ml of anhydrous tetrahydrofuran solution of 5.0 g (16.27 mmol) of the free form compound obtained in the step 2) of Example 12 were added 3.59 g (24.4 mmol) of phthalimide, 3.84 ml (24.4 mmol) of diethyl azodicarboxylate and 6.39 g (24.4 mmol) of triphenylphosphine, followed by stirring at room temperature for 10 hours. The reaction solution was concentrated under a reduced pressure and the resulting residue was subjected to a silica gel column chromatography, which wass eluted with ethyl acetate-n-hexane (1:1) to give 8.9 g of a mixture containing free form of the title compound. The resulting solid substance was pulverized, acidified by adding 1 N HCl, followed by addition of ethyl acetate and stirring for 1 hour. The thus precipitated crystals were collected by filtration to give 5.344 g of crude product. A 1.10 g portion of this was recrystallized from acetonitrile to give 724 mg of the title compound.

Melting point: 181–182° C.

$^1$H-NMR (δ ppm in DMSO-$d_6$) 11.13 (1H, br), 7.94 (1H, d), 7.90–7.83 (4H, m), 7.63 (1H, d), 6.66 (2H, d), 3.97 (2H, t), 3.36 (4H, m), 3.13 (2H, t), 1.84 (4H, m), 1.67–1.55 (4H, m)

EXAMPLE 35

1) Nα-Cyano-2-(hexahydro-1H-azepin-1-yl) methylthiophene-5-carboxamidine 3.68 g (68.08 mmol) of sodium methoxide was added to 210 ml of methanol solution containing 7.5 g (34.04 mmol) of 2-cyano-[5-[(hexahydro-1H-azepin-1-yl)methyl] thiophene, and the mixture was stirred at room temperature for 24 hours in an atmosphere of argon. To the reaction solution was added 3.9 ml (68.08 mmol) of acetic acid and 2.15 g (51.06 mmol) of cyanamide and again the mixture was stirred at room temperature for 24 hours. The reaction solution was concentrated, chloroform-methanol (20:1) was added to the resulting residue, followed by washing with water and drying over anhydrous magnesium sulfate. The solvent was evaporated and the resulting residue was subjected to a silica gel column chromatography, which was eluted with chloroform-methanol (50:1→10:1) to give 2.62 g of the title compound.

$^1$H-NMR (δ ppm in DMSO-$d_6$) 9.02 (1H, br), 8.49 (1H, br), 7.84 (1H, d), 7.01 (1H, d), 3.80 (2H, s), 2.59 (4H, br), 1.56 (8H, brs)

2) 1-[5-(3-Amino-1,2,4-oxadiazol-5-yl)-2-thenyl] hexahydro-1H-azepine 2.62 g (9.99 mmol) of the compound obtained in the above step 1) was dissolved in 55 ml of tetrahydrofuran and 11 ml of methanol, 1.41 g (19.98 mmol) of hydroxylamine hydrochloride and 4.23 ml (29.97 mmol) of triethylamine were added, and then the mixture was heated under reflux for 21 hours. The reaction solution was concentrated under a reduced pressure, chloroform-methanol (10:1) was added to the resulting residue, followed by washing with water and drying over anhydrous magnesium sulfate. The solvent was evaporated and the resulting residue was subjected to a silica gel column chromatography, which was eluted with chloroform-methanol (75:1) to give 2.58 g of the title compound.

Melting point: 135–136° C.

$^1$H-NMR (δ ppm in DMSO-d$_6$) 7.68 (1H, d), 7.09 (1H, d), 6.35 (2H, s), 3.87 (2H, s), 2.65–2.63 (4H, brs), 1.58 (8H, brs)

EXAMPLE 36

1-[5-(4-Amino-4H-1,2,4-triazol-3-yl)-2-thenyl] hexahydro-1H-azepine 2.0 g (9.08 mmol) of 2-cyano-[5-[(hexahydro-1H-azepin-1-yl)methyl]thiophene was dissolved in 13.5 ml of N,N-dimethylformamide, and 13.5 ml of hydrazine hydrate was added, followed by heating under reflux for 5 hours. After spontaneous cooling to room temperature, the reaction solution was poured into ice-water, and the thus precipitated crystals were collected by filtration, washed with water and then dried overnight at 70° C. under a reduced pressure to give 1.97 g of the title compound. A 560 mg portion of this compound was recrystallized from ethyl acetate to give 335 mg of the purified product.

Melting point: 104–105° C.

$^1$H-NMR (δ ppm in DMSO-d$_6$) 8.44 (1H, s), 7.72 (1H, d), 7.00 (1H, d), 6.34 (2H, s), 3.83 (2H, s), 2.64–2.62 (4H, m), 1.57 (8H, brs)

EXAMPLE 37

1) 4-Benzylimino-3-(5-[(hexahydro-1H-azepin-1-yl) methyl]-2-thienyl]-1,2,4-triazole 0.31 ml (3.0 mmol) of benzaldehyde was added to 10 ml of methanol solution containing 831 mg (3.0 mmol) of the compound of Example 36, and the mixture was stirred at room temperature for 4 hours. With ice-cooling, 827 mg (3.9 mmol) of NaBH(OAc)$_3$ and 0.35 ml of acetic acid were added, and the mixture was again stirred at room temperature for 9 days. The reaction solution was washed with saturated sodium bicarbonate aqueous solution and saturated brine and then dried over anhydrous magnesium sulfate. The solvent was evaporated under a reduced pressure and the resulting residue was subjected to a silica gel column chromatography, which was eluted with chloroform-methanol (25:1) to give 600 mg of the title compound.

$^1$H-NMR (δ ppm in CDCl$_3$) 8.63 (2H, d), 7.95 (2H, d), 7.84 (1H, d), 7.61–7.53 (3H, m), 6.95 (1H, d), 3.89 (2H, s), 2.71–2.69 (4H, m), 1.68–1.62 (8H, m)

2) 1-[5-(4-Benzylamino-4H-1,2,4-triazol-3-yl)-2-thenyl] hexahydro-1H-azepine

With ice-cooling, 58 mg (1.5 mmol) of sodium borohydride was added to 20 ml of ethanol solution containing 354 mg (0.969 mmol) of the compound obtained in the above step 1), and the mixture was stirred at room temperature for 24 hours. The reaction solution was concentrated, chloroform and aqueous ammonia were added to the resulting residue. Then, the resulting organic layer was separated and dried over anhydrous magnesium sulfate. The solvent was evaporated under a reduced pressure and the resulting residue was subjected to a silica gel column chromatography, which was eluted with chloroform-methanol-aqueous ammonia (100:10:1) to give 353 mg of the title compound.

Melting point: 79–81° C.

$^1$H-NMR (δ ppm in DMSO-d$_6$) 8.61 (1H, s), 7.67 (1H, d), 7.37–7.27 (5H, m), 7.19 (1H, t), 6.99 (1H, d), 4.22 (2H, d), 3.84 (2H, s), 2.65–2.62 (4H, m), 1.59 (8H, brs)

EXAMPLE 38

1) 2-(Hexahydro-1H-azepin-1-yl)methylthiophene-5-carboxylic acid amidinohydrazide 6.07 g (21.7 mmol) of S-methylisothiourea sulfate and 43.5 ml (43.5 mmol) of 1 N NaOH were added to 11.0 g (43.4 mmol) of 2-(hexahydro-1H-azepin-1-yl) methylthiophene-5-carboxylic acid hydrazide, methanol was added to the reaction mixture until it became uniform solution (about 130 ml) and then the resulting solution was stirred at room temperature for 10 days. After removing insoluble matter by filtration, the solvent was evaporated and the resulting residue was directly subjected to a silica gel column chromatography, which was eluted with chloroform-methanol-aqueous ammonia (40:10:1) to give 7.32 g of the title compound.

$^1$H-NMR (δ ppm in DMSO-d$_6$) 10.37 (1H, br), 7.13 (1H, d), 6.76 (1H, d), 6.73 (4H, br), 3.71 (2H, s), 2.59–2.57 (4H, m), 1.56 (8H, brs)

2) 1-[5-(5-Amino-1H-1,2,4-triazol-3-yl)-2-thenyl] hexahydro-1H-azepine 80 ml of ethanol solution containing 7.32 g (24.8 mmol) of the compound obtained in the above step 1) was heated under reflux for 8 days. The reaction solution was concentrated and the resulting residue was subjected to a silica gel column chromatography, which was eluted with chloroform-methanol-aqueous ammonia (100:10:1→40:10:1) to give 5.98 g of the title compound. A 1.5 g portion of this compound was recrystallized from 25 ml of acetonitrile to give 1.26 g of its crystals.

Melting point: 160–161° C.

$^1$H-NMR (δ ppm in DMSO-d$_6$) 11.95 (1H, brs), 7.20 (1H, brs), 6.86 (1H, brs), 6.04 (2H, brs), 3.76 (2H, s), 2.61–2.59 (4H, m), 1.56 (8H, brs)

EXAMPLE 39

5-Amino-N-benzyl-3-[5-[(hexahydro-1H-azepin-1-yl) methyl]-2-thienyl]-1H-1,2,4-triazole-1-carboxamide 5 ml of N,N-dimethylformamide solution containing 331 mg (2.49 mmol) of benzyl isocyanate was added to 75 ml of N,N-dimethylformamide solution containing 690 mg (2.49 mmol) of the compound of Example 38, and the mixture was stirred at room temperature for 2 hours. The reaction solution was concentrated, and the resulting residue was dissolved in chloroform, washed with water and then dried over anhydrous magnesium sulfate. The solvent was evaporated and the resulting residue was subjected to a silica gel column chromatography, which was eluted with chloroform-methanol (75:1) to give 1.07 g of the title compound. This was crystallized by adding an appropriate amount of diethyl ether and then recrystallized from ethyl acetate-n-hexane to give 564 mg of the compound of interest.

Melting point: 130–131° C.

$^1$H-NMR (δ ppm in DMSO-d$_6$) 7.45 (1H, d, J=3.7 Hz), 7.40–7.31 (5H, m), 7.24 (1H, t), 6.84 (1H, d, J=3.7 Hz), 6.27 (2H, brs), 4.57 (2H, d, J=6.1 Hz), 3.83 (2H, s), 2.68–2.66 (4H, m), 1.65–1.60 (8H, m)

EXAMPLE 40

1) Ethyl-N$^1$-[5-[(hexahydro-1H-azepin-1-yl)methyl]-2-thienoyl] -N$^2$-oxamidrazonate 7.4 ml (52.5 mmol) of triethylamine was added to 150 ml of anhydrous dichloromethane solution containing carboethoxy—S—methylthioformimidium tetrafluoroborate (30.86 mmol) and 6.33 g (25.0 mmol) of 2-(hexahydro-1H-azepin-1-yl)methylthiophene-5-carboxylic acid hydrazide, and the mixture was heated under reflux for 36 hours. The reaction solution was washed with water and then dried over anhydrous magnesium sulfate. The solvent was evaporated and the resulting residue was subjected to a silica gel column chromatography to give 5.70 g of the title compound.

$^1$H-NMR (δ ppm in CDCl$_3$) 11.45 (1H, br), 8.10 (1H, d), 6.94 (1H, d), 6.12 (2H, br), 4.38 (2H, m), 3.87 (2H, s), 2.66 (4H, m), 1.62 (8H, br), 1.45 (3H, t)

2) Ethyl-3-[5-[(hexahydro-1H-azepin-1-yl)methyl]-2-thienyl]-1H-1,2,4-triazole-5-carboxylate 352 mg (1.0 mmol) of the compound obtained in the above step 1) was dissolved in 5 ml of acetic acid, and the solution was heated under reflux for 3 hours. The reaction solution was concentrated under a reduced pressure, aqueous ammonia and chloroform were added to the resulting residue, and the resulting organic layer was separated and dried over anhydrous magnesium sulfate. Then, the solvent was evaporated, and the resulting residue was subjected to a silica gel column chromatography to give 248 mg of the title compound.

$^1$H-NMR (δ ppm in CDCl$_3$) 7.51 (1H, d), 6.85 (1H, d), 4.45–4.29 (2H, m), 3.96 (2H, brs), 2.81 (4H, br), 1.61 (8H, br), 1.33 (3H, t) MS (FAB, Pos, m/z) 335 (M++1)

EXAMPLE 41

5-[5-[(Hexahydro-1H-azepin-1-yl)methyl]-2-thienyl]-1H-1,2,4-triazole-3-methanol

With ice-cooling, 20 ml of anhydrous tetrahydrofuran solution containing 502 mg (1.5 mmol) of the compound of Example 40 was added dropwise to 5 ml of anhydrous tetrahydrofuran suspension of 85.4 mg (2.25 mmol) lithium aluminum hydride, and the mixture was stirred at the same temperature for 4 hours. Sodium sulfate decahydrate was added to the reaction mixture, the resulting insoluble matter was removed by filtration, the solvent was evaporated and then the resulting residue was subjected to a silica gel column chromatography, which was eluted with chloroform-methanol (10:1) to give 312 mg of the title compound.

Melting point: 159–161° C.

$^1$H-NMR (δ ppm in DMSO-d$_6$) 13.89 (1H, br), 7.37 (1H, d), 6.93 (1H, d), 5.62 (1H, br), 4.57 (2H, d), 3.81 (2H, s), 2.63–2.60 (4H, m), 1.57 (8H, brs)

EXAMPLE 42

1-[5-(5-Methyl-1H-1,2,4-triazol-3-yl]-2-thenyl) hexahydro-1H-azepine dihydrochloride To 5 ml of ethanol solution containing 1.01 g (4.0 mmol) of 2-(hexahydro-1H-azepin-1-yl)methylthiophene-5-carboxylic acid hydrazide was added 2.8 ml (20 mmol) of triethylamine and 2.48 g (20 mmol) of ethyl acetoimidate hydrochloride, and the mixture was stirred at room temperature for 21 hours. Then, 1.2 g of ammonium chloride was added and the mixture was stirred at 80° C. for 4 hours. The reaction solution was concentrated, 28% aqueous ammonia and chloroform were added to the resulting residue, and then the resulting organic layer was separated and dried over anhydrous magnesium sulfate. The solvent was evaporated and the resulting residue was subjected to a silica gel column chromatography, which was eluted with chloroform-methanol (80:1) to give 814 mg of the title compound in its free form. By subjecting this compound to salt formation using 4 N HCl/ethyl acetate, 593 mg of the title compound was obtained.

Melting point: 161–163° C.

$^1$H-NMR (δ ppm in DMSO-d$_6$) 11.06 (1H, br), 7.59 (1H, d), 7.45 (1H, d), 4.56–4.55 (2H, d), 3.38–3.33 (2H, m), 3.10–3.02 (2H, m), 2.39 (3H, s), 1.85–1.83 (4H, m), 1.68–1.63 (2H, m), 1.60–1.54 (2H, m)

EXAMPLE 43

1-[5-(5-Amino-1,3,4-oxadiazol-2-yl)-2-thenyl] hexahydro-1H-azepine 2.5 g (23.57 mmol) of cyanogen bromide was added to 250 ml of ethanol solution containing 5.43 g (21.43 mmol) of 2-(hexahydro-1H-azepin-1-yl)methylthiophene-5-carboxylic acid hydrazide, and the mixture was stirred at room temperature for 2 hours and then at 50° C. for 7 hours. The reaction solution was concentrated under a reduced pressure, saturated sodium bicarbonate aqueous solution and chloroform were added to the resulting residue. Then, the resulting organic layer was separated, washed with saturated brine and then dried over anhydrous magnesium sulfate. The solvent was evaporated and the resulting residue was recrystallized from ethyl acetate to give 2.43 g of the title compound.

Melting point: 232–234° C.

$^1$H-NMR (δ ppm in DMSO-d$_6$) 7.33 (1H, d), 7.23 (2H, s), 7.00 (1H, d), 3.83 (2H, s), 2.63–2.61 (4H, m), 1.57 (8H, brs)

EXAMPLE 44

1-Benzyl-3-[5-[5-[(hexahydro-1H-azepin-1-yl)methyl]-2-thienyl]-1,3,4-oxadiazol-2-yl]urea 0.14 ml (1.1 mmol) of benzyl isocyanate was added to 20 ml of pyridine solution containing 278 mg (1.0 mmol) of the compound of Example 43, and the mixture was stirred at room temperature for 24 hours. The reaction solution was concentrated under a reduced pressure, and the resulting residue was subjected to a silica gel column chromatography, which was eluted with chloroform-methanol (50:1) to give 406 mg of the title compound.

Melting point: 184–185° C.

$^1$H-NMR (δ ppm in DMSO-d$_6$) 10.96 (1H, br), 7.97 (1H, t), 7.48 (1H, d, J 3.7 Hz), 7.37–7.24 (5H, m), 7.07 (1H, d, J=3.7 Hz), 4.41 (2H, d, J=5.7 Hz), 3.86 (2H, s), 2.64 (4H, brs), 1.58 (8H, brs)

EXAMPLE 45

1) 4-[5-[(Hexahydro-1H-azepin-1-yl)methyl]-2-thienyl]-1-benzyl thiosemicarbazide 5 ml of ethanol solution containing 928 mg (6.22 mmol) of benzyl isothiocyanate was added dropwise to 15 ml of ethanol solution containing 1.5 g (5.92 mmol) of 2-(hexahydro-1H-azepin-1-yl)methylthiophene-5-carboxylic acid hydrazide, and the mixture was stirred at room temperature for 2 hours and then heated under reflux for 1 hour. The reaction solution was cooled with ice-water, and the thus precipitated crystals were collected by filtration, washed thoroughly with cold ethanol and then dried under a reduced pressure to give 2.19 g of the title compound.

$^1$H-NMR (δ ppm in DMSO-d$_6$) 8.06 (1H, t), 7.94 (1H, d), 7.32–7.22 (6H, m), 5.23 (2H, s), 4.26–4.22 (4H, m), 2.92 (4H, brs), 1.70 (4H, brs), 1.59 (4H, brs)

2) 1-(5-(5-Amino-1,3,4-thiadiazol-2-yl)-2-thenyl] hexahydro-1H-azepine 6 ml of concentrated sulfuric acid was added to 806 mg (2.0 mmol) of the compound obtained in the above step 1), and the mixture was stirred as such for 1 hour and then at room temperature for 3 hours. The reaction solution was poured into ice, alkalified with 5 N sodium hydroxide aqueous solution and then extracted with ethyl acetate. The resulting organic layer was dried over anhydrous magnesium sulfate, the solvent was evaporated and then the resulting residue was recrystallized from ethyl acetate-n-hexane to give 482 mg of the title compound.

Melting point: 156–157° C.

$^1$H-NMR (δ ppm in CDCl$_3$) 7.17 (1H, d, J=3.9 Hz), 6.83 (1H, d, J=3.9 Hz), 5.44 25 (2H, brs), 3.83 (2H, s), 2.69–2.66 (4H, m), 1.65–1.62 (8H, m)

EXAMPLE 46

1-Benzyl-3-[5-[5-[(hexahydro-1H-azepin-1-yl)methyl]-2-thienyl]-1,3,4-thiadiazol-2-yl]urea 5 ml of N,N-dimethylformamide solution containing 132 mg (1.16 mmol) of benzyl isocyanate was added dropwise to 25 ml of N,N-dimethylformamide solution containing 342 mg (1.16 mmol) of the compound obtained in the step 2) of Example 45, and the mixture was stirred at room temperature for 22 hours. The reaction solution was concentrated under a reduced pressure, chloroform and water were added to the resulting residue, and then the resulting organic layer was separated and dried over anhydrous magnesium sulfate. The solvent was evaporated and the resulting residue was subjected to a silica gel column chromatography, which was eluted with chloroform-methanol (40:1 25:1) to give 399 mg of the title compound.

Melting point: 232–233° C.

$^1$H-NMR (δ ppm in DMSO-d$_6$) 11.13 (1H, br), 7.41 (1H, d, J=3.7 Hz), 7.36–7.25 (5H, m), 7.16 (1H, brs), 6.98 (1H, d, J=3.7 Hz), 4.37 (2H, d, J=6.1 Hz), 3.82 (2H, s), 2.64–2.62 (4H, m), 1.58 (8H, br)

EXAMPLE 47

N-[5-[5-[(Hexahydro-1H-azepin-1-yl)methyl]-2-thienyl]-1,3,4-thiadiazol-2-yl]benzamide In the same manner as described in Example 10, 396 mg of the title compound was obtained using 350 mg (1.19 mmol) of the compound obtained in the step 2) of Example 45, 0.33 ml (2.38 mmol) of triethylamine, 0.18 mg (1.55 mmol) of benzoyl chloride and a catalytically effective amount of 4-N,N-dimethylaminopyridine.

Melting point: 219–221° C.

$^1$H-NMR (δ ppm in DMSO-d$_6$) 13.04 (1H, br), 8.14 (2H, d), 7.66 (1H, d), 7.59–7.56 (3H, m), 7.04 (1H, d), 3.88 (2H, s), 2.68–2.66 (4H, m), 1.60 (8H, m)

EXAMPLE 48

1-[5-(5-Benzylamino-1,3,4-thiadiazol-2-yl)-2-thenyl]hexahydro-1H-azepine 0.37 ml (3.67 mmol) of benzaldehyde was added dropwise to 100 ml of 1,2-dichloroethane solution containing 1.08 g (3.67 mmol) of the compound obtained in the step 2) of Example 45, and the mixture was stirred at room temperature for 90 minutes, 1.02 g (7.34 mmol) of NaBH(OAc)$_3$ and 0.42 ml (7.34 mmol) of acetic acid were added, and the mixture was then stirred again at room temperature for 51 hours. The reaction solution was washed with saturated sodium bicarbonate aqueous solution and saturated brine in that order and then dried over anhydrous magnesium sulfate. The solvent was evaporated under a reduced pressure and the resulting residue was purified by a silica gel column chromatography to give 270 mg of the title compound.

Melting point: 165–166° C.

$^1$H-NMR (δ ppm in DMSO-d$_6$) 8.40 (1H, t), 7.38–7.26 (5H, m), 7.22 (1H, d, J=3.7 Hz), 6.93 (1H, d, J=3.7 Hz), 4.52 (2H, d, J=5.5 Hz), 3.79 (2H, s), 2.62–2.60 (4H, m), 1.57 (8H, br)

EXAMPLE 49

1-[5-(5-Ethylamino-1,3,4-thiadiazol-2-yl)-2-thenyl]hexahydro-1H-azepine

In the same manner as described in Example 45, 820 mg of the title compound was obtained from 760 mg (3.0 mmol) of 2-(hexahydro-1H-azepin-1-yl)methyl)methylthiophene-5-carboxylic acid hydrazide and 288 mg (3.3 mmol) of ethyl isothiocyanate.

Melting point: 112–114° C.

$^1$H-NMR (δ ppm in DMSO-d$_6$) 7.88 (1H, t), 7.22 (1H, d), 6.93 (1H, d), 3.80 (2H, s), 3.34–3.29 (2H, s), 2.63–2.61 (4H, m), 1.57 (8H, br), 1.20 (3H, t)

EXAMPLE 50

1-Ethyl-3-[5-[5-[(hexahydro-1H-azepin-1-yl)methyl]-2-thienyl]-1,3,4-thiadiazol-2-yl]urea In the same manner as described in Example 46, 220 mg of the title compound was obtained from 200 mg (0.68 mmol) of the compound obtained in the step 2) of Example 45 and 51 mg (0.72 mmol) of ethyl isocyanate.

Melting point: 203–204° C.

$^1$H-NMR (δ ppm in DMSO-d$_6$) 10.99 (1H, brs), 7.41 (1H, d, J=3.7 Hz), 6.98 (1H, d, J =3.7 Hz), 6.62 (1H, brs), 3.82 (2H, s), 3.21–3.15 (2H, m), 2.64–2.62 (4H, m), 1.58 (8H, brs), 1.08 (3H, t, J =6.7 Hz)

EXAMPLE 51

N-[5-[5-[(Hexahydro-1H-azepin-1-yl)methyl]-2-thienyl]-1,3,4-thiadiazol-2-yl]acetamide In the same manner as described in Example 47, 380 mg of the title compound was obtained from 350 mg (1.19 mmol) of the compound obtained in the step 2) of Example 45 and 0.15 ml of acetic anhydride.

Melting point: 248–249° C.

$^1$H-NMR (δ ppm in DMSO-d$_6$) 12.61 (1H, br), 7.52 (1H, d, J=3.7 Hz), 7.0 (1H, d, J=3.7 Hz), 3.83 (2H, s), 3.64–3.62 (4H, m), 2.21 (3H, s), 1.58 (8H, brs)

EXAMPLE 52

1) 5-[(Hexahydro-1H-azepin-1-yl)methyl]-thiophene-5-N-methoxy-N-methyl carboxamide 8.0 g (29.0 mmol) of 2-(hexahydro-1H-azepin-1-yl) methylthiophene-5-carboxylic acid hydrochloride was suspended in 300 ml of tetrahydrofuran, 10.1 ml (72.5 mmol) of triethylamine, 4.12 g (30.46 mmol) of hydroxybenzotriazole and 8.34 g (43.5 mmol) of WSCDΩHCl were added, and the mixture was stirred at room temperature for 1 hour. Then, 3.51 g (36.0 mmol) of N,O-dimethylhydroxylamine hydrochloride and 8.36 ml (60.0 rnmol) of triethylamine were added, followed by stirring overnight. To the reaction solution was added ethyl acetate and water, and the resulting organic layer was separated and dried over anhydrous magnesium sulfate. The solvent was evaporated and the resulting residue was subjected to a silica gel column chromatography, which was eluted with chloroform-methanol (80:1) to give 7.51g of the title compound.

$^1$H-NMR (δ ppm in CDCl$_3$) 1.63 (8H, brs), 2.68 (4H, m), 3.35 (3H, s), 3.84 (3H, s), 3.85 (2H, s), 6.89 (1H, d, J=3.7 Hz), 7.80 (1H, d, J =3.7 Hz)

2) 2-Acetyl-5-[(hexahydro-1H-azepin-1-yl)methyl]thiophene

In a stream of argon and at 0° C., 39.0 ml (40.4 mmol) of methyl lithium (1.04 M solution in diethyl ether) was added dropwise to 70 ml of anhydrous tetrahydrofuran solution containing 9.51 g (33.68 mmol) of the compound obtained in the above step 1), and the mixture was stirred at the same temperature for 30 minutes and then at room temperature for 3 hours. To the reaction solution was added water and ethyl acetate, and the resulting organic layer was separated and dried over anhydrous magnesium sulfate. The solvent was evaporated under a reduced pressure and the resulting residue was subjected to a silica gel column chromatography, which was eluted with chloroform-methanol (80:1) to give 7.10 g of the title compound.

$^1$H-NMR ($\delta$ ppm in CDCl$_3$) 7.55 (1H, d), 6.91 (1H, d), 3.83 (2H, d), 2.67–2.55 (4H, m), 2.52 (3H, s), 1.62 (8H, br)

3) (E)-N-[1-[5-[(Hexahydro-1H-azepin-1-yl)methyl]-2-thienyl]-ethylidene]-4H-1,2,4-triazole-4-amine 1.93 g (22.95 mmol) of 4-amino-1,2,4-triazole and a catalytically effective amount of p-toluenesulfonic acid were added to 50 ml of toluene solution containing 1.19 g (5.0 mmol) of the compound obtained in the above step 2), and the mixture was heated under reflux for 1 week in an apparatus equipped with a Dean Stark tube. The reaction solution was washed with saturated sodium bicarbonate aqueous solution and saturated brine in that order and dried over anhydrous magnesium sulfate and then the solvent was evaporated under a reduced pressure to give 1.28 g of the title compound.

$^1$H-NMR ($\delta$ ppm in CDCl$_3$) 8.21 (2H, s), 7.48 (1H, d, J=4.0 Hz), 7.94 (1H, d, J=4.0 Hz), 3.85 (2H, s), 2.69–2.65 (4H, m), 2.35 (3H, s), 1.64 (8H, br)

4) (E,E)-N-[3-Dimethylamino-1-[5-[(hexahydro-1H-azepin-1-yl)methyl]-2-thienyl]-2-propylidene-4H-1,2,4-triazole-4-amine 2.76 ml (13.38 mmol) of tert-butoxybis(dimethylamine)methane (Bradereck's reagent) was added dropwise to 50 ml of tetrahydrofuran solution containing 1.23 g (4.05 mmol) of the compound obtained in the above step 3), and the mixture was stirred at room temperature for 48 hours in an atmosphere of argon. The reaction solution was concentrated under a reduced pressure to give 1.38 g of the title compound.

$^1$H-NMR ($\delta$ ppm in CDCl$_3$) 8.23 (2H, s), 7.3–6.90 (3H, m), 4.74 (1H, d), 3.86 (2H, s), 2.89 (6H, s), 2.70–2.64 (4H, m), 1.63 (8H, br)

5) 6-[5-[(Hexahydro-1H-azepin-1-yl)methyl]-2-thienyl]-1,2,4-triazolo[4,3-b]pyridazine A 717 mg (2.0 mmol) of the compound obtained in the above step 4) was dissolved in 20 ml of acetic acid and the mixture was heated under reflux for 4 hours. The reaction solution was concentrated under a reduced pressure, and saturated sodium bicarbonate aqueous solution and chloroform were added to the residue. The resulting organic layer was separated, washed with saturated brine and then dried over anhydrous magnesium sulfate. The solvent was evaporated and the resulting residue was subjected to a silica gel column chromatography, which was eluted with acetone-toluene (2:1) to give 690 mg of the title compound. By recrystallizing this compound from ethyl acetate-isopropyl ether, 174 mg of the desired compound was obtained.

Melting point: 101–102° C.

$^1$H-NMR ($\delta$ ppm in CDCl$_3$) 9.06 (1H, s), 8.09 (1H, d), 7.54 (1H, d), 7.49 (1H, d), 6.96 (1H, d), 3.88 (2H, s), 2.73–2.70 (4H, m), 1.68–1.59 (8H, m)

EXAMPLE 53

1) N,N-Dimethyl-N'-[5-[(hexahydro-1H-azepin-1-yl)methyl]-2-thienyl]-formamidine 3.72 g (15.65 mmol) of 5-[(hexahydro-1H-azepin-1-yl)methyl]thiophene-2-carboxamide was dissolved in 30 ml of N,N-dimethylformamide, 3.4 ml (25.6 mmol) of N,N-dimethylformamide dimethylacetal was added, and the mixture was stirred at 80° C. for 4 hours. The reaction solution was concentrated under a reduced pressure, and the resulting residue was dissolved in chloroform, washed with water and then dried over anhydrous magnesium sulfate. By evaporating the solvent, 3.82 g of the title compound was obtained.

$^1$H-NMR ($\delta$ ppm in CDCl$_3$) 8.58 (1H, s), 7.73 (1H, d), 6.88 (1H, d), 3.85 (2H, s), 3.19 (6H, s), 2.71–2.62 (4H, m), 1.62 (8H, brs)

2) 1-[5-(1,2,4-Oxadiazol-5-yl)-2-thenyl]hexahydro-1H-azepine 1.0 oxalate 0.9 ml (11.0 mmol) of pyridine and 1.64 g (14.5 mmol) of hydroxylamine o-sulfonate were added to 20 ml of methanol solution containing 1.91 g (7.25 mmol) of the compound obtained in the above step 1), and the mixture was stirred overnight at room temperature. The reaction solution was concentrated under a reduced pressure, 10% K$_2$CO$_3$ aqueous solution was added to the residue while cooling with water, and the mixture was extracted with chloroform. Then, the resulting organic layer was washed with saturated brine and dried over anhydrous magnesium sulfate. The solvent was evaporated under a reduced pressure and the resulting residue was subjected to a silica gel column chromatography, which was eluted with chloroform-methanol (100:1~80:1) to give 42 mg of the title compound in its free form. A 40 mg portion of the free form compound was dissolved in 5 ml of methanol and 2 ml of chloroform, methanol solution containing 13 mg of oxalic acid was added, and the mixture was concentrated under a reduced pressure. Then, the resulting residue was crystallized from methanol and diethyl ether to give 33 mg of the title compound.

Melting point: 131–132° C.

$^1$H-NMR ($\delta$ ppm in DMSO-d$_6$) 9.48 (1H, br), 7.37 (1H, d), 7.19 (1H, d), 4.51 (2H, s), 3.14 (1H, br), 3.10 (1H, br), 1.80 (2H, m), 1.60 (4H, m)

EXAMPLE 54

1-[5-(1H-1,2,4-triazol-3-yl)-2-thenyl]hexahydro-1H-azepine 0.15 ml (3.0 mmol) of hydrazine hydrate was added dropwise to 3.5 ml of acetic acid solution containing 440 mg (1.5 mmol) of the compound obtained in the step 1) of Example 53, and the mixture was stirred at room temperature for 120 hours and then at 80° C. for 4 hours. The reaction solution was concentrated under a reduced pressure, 28% aqueous ammonia and chloroform were added, and then the resulting organic layer was separated and dried over anhydrous magnesium sulfate. The solvent was evaporated under a reduced pressure and the resulting residue (333 mg) was recrystallized from ethyl acetate to give 99 mg of the title compound.

Melting point: 129–130° C.

$^1$H-NMR ($\delta$ ppm in DMSO-d$_6$) 9.11 (1H, s), 7.42 (1H, d), 6.95 (1H, d), 3.80 (2H, s), 2.63–2.61 (4H, m), 1.57 (8H, brs)

EXAMPLE 55

1) 5-[(Hexahydro-1H-azepin-1-yl)methyl]-2-thiophene amidoxime 19 g of hydroxylamine hydrochloride was added to 500 l of ethanol solution containing 70 g of 2-cyano-[5-(hexahydro-1H-azepin-1-yl)methyl]thiophene, and the mixture was stirred at 80° C. for 5 hours. The reaction solution was concentrated, 500 ml of saturated sodium bicarbonate aqueous solution was added, and then the mixture was extracted three times with 300 ml of chloroform. The resulting organic layers were combined, washed with saturated brine, dried over anhydrous sodium sulfate and concentrated under a reduced pressure. The resulting residue was purified by a silica gel column chromatography to give 51 g of the title compound.

$^1$H-NMR (δ ppm in CDCl$_3$) 1.61 (8H, s), 2.50–2.80 (4H, m), 3.82 (2H, s), 4.56 (2H, br), 6.82 (1H, d), 7.10 (1H, d), 7.27 (1H, br)

2) Ethyl 3-[5-[(hexahydro-1H-azepin-1-yl)methyl]-2-thienyl]-1,2,4-oxadiazole-5-carboxylate hydrochloride With ice-cooling, 0.5 ml of triethylamine and 0.4 ml of ethyl chloroglyoxylate were added to 20 ml of chloroform solution containing 831 mg of the compound obtained in the step 1) of Example 55, and the mixture was stirred at 40° C. for 3 hours. To the reaction solution was added 50 ml of saturated sodium bicarbonate aqueous solution to effect separation of layers, and the resulting organic layer was dried over anhydrous sodium sulfate and concentrated under a reduced pressure. The resulting residue was purified by a silica gel column chromatography, 4 N hydrochloric acid-ethyl acetate was added, and then the thus precipitated crystals were collected by filtration to give 370 mg of the title compound.

Melting point: 178–179° C.

$^1$H-NMR (δ ppm in DMSO-d$_6$) 1.37 (3H, t), 1.50–1.90 (8H, m), 3.05–3.20 (2H, m), 3.35–3.50 (2H, m), 4.46 (2H, q), 4.67 (2H, d), 7.53 (1H, d), 7.91 (1H, d), 10.05 (1H, br)

EXAMPLE 56

1) 1-[5-(5-t-Butyldimethylsilyloxymethyl-1,2,4-oxadiazol-3-yl)-2-thenyl]hexahydro-1H-azepine 220 mg of sodium hydride was added to 50 ml of tetrahydrofuran solution containing 2.1 g of the compound obtained in the step 1) of Example 55, and the mixture was stirred at room temperature for 1 hour, 1.8 g of ethyl 2-t-butyldimethylsilyloxyacetate was added, and then the mixture was stirred at 60° C. for 3 hours. To the reaction solution was added 200 ml of saturated brine and the mixture was extracted three times with 100 ml of ethyl acetate. The resulting organic layers were combined, washed with saturated brine, dried over anhydrous sodium sulfate and concentrated under a reduced pressure. The resulting residue was purified by a silica gel column chromatography to give 1.1 g of the title compound.

$^1$H-NMR (δ ppm in CDCl$_3$) 0.03 (6H, s), 0.78 (9H, s), 1.04–1.60 (8H, m), 2.40–2.60 (4H, m), 3.70 (2H, s), 4.78 (2H, s), 6.75 (1H, d), 7.46 (1H, d)

2) 1-[5-(5-Hydroxymethyl-1,2,4-oxadiazol-3-yl)-2-thenyl] hexahydro-1H-azepine hydrochloride 4.0 ml of 1.0 N tetrabutylammonium fluoride-tetrahydrofuran solution was added to 10 ml of tetrahydrofuran solution containing 1.1 g of 1-[5-[(5-t-butyldimethylsilyloxymethyl-1,2,4-oxadiazol-3-yl)-2-thenyl]hexahydro-1H-azepine, and the mixture was stirred at room temperature for 2 hours. The reaction solution was concentrated under a reduced pressure, the resulting residue was purified by a silica gel column chromatography. Then, 4 N hydrochloric acid-ethyl acetate was added and the thus precipitated crystals were collected by filtration to give 680 mg of the title compound.

Melting point: 171–172° C.

$^1$H-NMR (δ ppm in DMSO-d$_6$) 1.50–1.75 (4H, m), 1.75–1.90 (4H, s), 3.00–3.20 (2H, m), 3.30–3.45 (2H, m), 4.63 (2H, d), 4.79 (2H, s), 6.11 (1H, br), 7.55 (1H, d), 7.79 (1H, d), 10.74 (1H, br)

EXAMPLE 57

1) 1-[5-(5-t-Butoxycarbonylaminomethyl-1,2,4-oxadiazol-3-yl)-2-thenyl]hexahydro-1H-azepine Using 1.7 g of 5-(hexahydro-1H-azepin-1-yl)methyl-2-thiopheneamidoxime and 2.0 g of N-t-butoxycarbonylglycine ethyl ester, 1.1 g of the title compound was obtained in the same manner as described in the step 1) of Example 56.

$^1$H-NMR (δ ppm in CDCl$_3$) 1.47 (9H, s), 1.63 (8H, br), 2.50–2.80 (4H, m), 3.86 (2H, d), 4.58 (2H, d), 5.20 (1H, br), 6.91 (1H, d), 7.61 (1H, d)

2) 1-[5-(5-Aminomethyl-1,2,4-oxadiazol-3-yl)-2-thenyl] hexahydro-1H-azepine dihydrochloride ½ hydrate 1.1 g of 1-[5-(5-t-butoxycarbonylaminomethyl-1,2,4-oxadiazol-3-yl)-2-thenyl]hexahydro-1H-azepine was dissolved in 30 ml of 4 N hydrochloric acid-1,4-dioxane solution, and the solution was stirred at room temperature for 30 minutes. The reaction solution was concentrated under a reduced pressure, and the resulting residue was recrystallized from ethyl acetate to give 966 mg of the title compound.

Melting point: 203–204° C.

$^1$H-NMR (δ ppm in DMSO-d$_6$) 1.50–1.75 (4H, br), 1.85 (4H, s), 3.00–3.20 (2H, br), 3.30–3.50 (2H, br), 4.58 (2H, s), 4.63 (2H, s), 7.58 (1H, d), 7.81 (1H, d), 8.94 (3H, br), 11.22 (1H, br)

EXAMPLE 58

Ethyl 2-[3-[5-[(hexahydro-1H-azepin-1-yl)methyl]-2-thienyl]-1,2,4-oxazol-5-yl]acetate hydrochloride 3.6 g of diethyl malonate was added to 100 ml of toluene solution containing 2.0 g of 5-[(hexahydro-1H-azepin-1-yl) methyl)-thiophene-2-amidoxime, and the mixture was stirred overnight at 100° C. The reaction solution was concentrated under a reduced pressure, the resulting residue was purified by a silica gel column chromatography. Then, 4 N hydrochloric acid-ethyl acetate and the resulting precipitate was recrystallized from ethanol-diethyl ether to give 1.6 g of the title compound.

(Yield, 53%)

Melting point: 122–123° C.

$^1$H-NMR (δ ppm in CDCl$_3$) 1.22 (3H, t), 1.50–1.70 (4H, m), 1.75–1.90 (4H, m), 3.00–3.15 (2H, m), 3.30–3.45 (2H, m), 4.17 (2H, q), 4.37 (2H, s), 4.65 (2H, d), 7.53 (1H, d), 7.81 (1H, d), 10.34 (1H, br)

EXAMPLE 59

1-[5-(5-Hydroxyethyl-1,2,4-oxadiazol-3-yl)-2-thenyl] hexahydro-1H-azepine hydrochloride With ice-cooling, 650 mg of sodium borohydride was added to 40 ml of THF solution containing 1.5 g of free base ethyl 2-[3-[5-[(hexahydro-1H-azepin-1-yl)methyl]-2-thienyl]-1,2,4-oxazol-5-yl]acetate, 27 ml of methanol was added to the resulting mixture spending about 1 hour with stirring, and the stirring was continued for additional 1 hour. With ice-cooling, 1 N hydrochloric acid was added to the reaction solution until bubbling ceased, then 100 ml of saturated sodium bicarbonate was added, and the mixture was extracted three times with 50 ml of chloroform. The organic layers were combined, washed with saturated brine, dried over anhydrous sodium sulfate and concentrated under a reduced pressure, the resulting residue was purified by a silica gel column chromatography, 4 N hydrochloric acid-ethyl acetate was added, and then the thus precipitated crystals were collected by filtration and recrystallized from ethanol-ethyl acetate to give 725 mg of the title compound.

Melting point: 186–187° C.

$^1$H-NMR (δ ppm in DMSO-$d_6$) 1.50–1.70 (4H, m), 1.75–1.90 (4H, m), 3.00–3.20 (4H, m), 3.30–3.40 (2H, m), 3.85 (2H, t), 4.65 (2H, d), 7.51 (1H, d), 7.78 (1H, d), 10.27 (1H, br)

EXAMPLE 60

1) 1-[5-(5-t-Butoxycarbonylaminoethyl-1,2,4-oxadiazol-3-yl)-2-thenyl]hexahydro-1H-azepine dihydrochloride Using 2.9 g of 5-[(hexahydro-1H-azepin-1-yl)methyl]-2-thiophene amidoxime and 2.0 g of N-t-butoxycarbonyl-β-alanine methyl ester, 1.2 g of the title compound was obtained in the same manner as described in Example 56.

$^1$H-NMR (δ ppm in CDCl$_3$) 1.44 (9H, s), 1.63 (8H, s), 2.55–2.80 (4H, m), 3.11 (2H, t), 3.60 (2H, t), 3.86 (2H, s), 5.15 (1H, br), 6.91 (1H, d), 7.61 (1H, d)

2) 1-[5-(5-Aminoethyl-1,2,4-oxadiazol-3-yl)-2-thenyl]hexahydro-1H-azepine

Using 1.1 g of 1-[5-(5-t-butoxycarbonylaminoethyl1,2,4-oxadiazol-3-yl)-2-thenyl]hexahydro-1H-azepine, 1.1 g of the title compound was obtained by carrying out its deprotection in the same manner as described in the step 2) of Example 57.

Melting point: 210–211° C.

$^1$H-NMR (δ ppm in DMSO-$d_6$) 1.50–1.75 (4H, m), 1.84 (4H, s), 2.40–2.60 (2H, t), 3.10–3.20 (2H, t), 3.40–3.50 (4H, m), 4.63 (2H, d), 7.56 (1H, d), 7.80 (1H, d), 8.15 (3H, br), 11.00 (1H, br)

EXAMPLE 61

1) 5-[(Hexahydro-1H-azepin-1-yl)methyl]-2-thiophene carbothioamide 3 ml of triethylamine was added to 50 ml of pyridine solution containing 4.6 g of 1-(5-cyano-2-thenyl)hexahydro-1H-azepine and, while stirring at room temperature, hydrogen sulfide gas was bubbled into the mixture in small portions spending 2 hours. The reaction solution was concentrated under a reduced pressure, 50 ml of saturated sodium bicarbonate aqueous solution was added to the resulting residue, and the mixture was extracted three times with 50 ml of chloroform. The organic layers were combined, washed with saturated brine, dried over anhydrous sodium sulfate and then concentrated under a reduced pressure, and the resulting residue was purified by a silica gel column chromatography to give 4.3 g of the title compound.

$^1$H-NMR (δ ppm in DMSO-$d_6$) 1.56 (8H, s), 2.45–2.75 (4H, m), 3.74 (2H, s), 6.94 (1H, d), 7.54 (1H, d), 9.30 (1H, br), 9.47 (1H, br)

2) 1-(5-(4-Methylthiazol-2-yl)-2-thenyl]hexahydro-1H-azepine dihydrochloride 730 mg of chloroacetone was added to 30 ml of ethanol solution containing 2.0 g of 5-[(hexahydro-1H-azepin-1-yl)methyl]-2-thiophenecarbothioamide, and the mixture was stirred overnight at 80° C. The reaction solution was ice-cooled, adjusted to pH 1 by adding hydrochloric acid and then concentrated under a reduced pressure. The resulting residue was then recrystallized from acetonitrile to give 1.6 g of the title compound.

Melting point: 187–190° C.

$^1$H-NMR (δ ppm in DMSO-$d_6$) 1.50–2.00 (8H, m), 2.38 (3H, s), 3.00–3.20 (2H, m), 3.35–3.45 (2H, m), 4.54 (2H, s), 7.32 (1H, s), 7.46 (1H, d), 7.58 (1H, d), 7.70 (1H, br), 11.36 (1H, br)

EXAMPLE 62

1) 2-[5-Phthalimidomethyl-2-thienyl]imidazo[1,2-a]pyridine

5-Bromoacetyl-2-(phthalimidomethyl)thiophene (0.80 g) and 2-aminopyridine (0.23 g) were dissolved in anhydrous ethanol (50 ml) and heated under reflux for 6 hours. The resulting crystals were collected by filtration and purified by a silica gel column chromatography (chloroform:methanol= 100:1) to give 0.38 g of the title compound.

$^1$H-NMR (δ ppm in DMSO-$d_6$) 8.48 (1H, d), 8.24 (1H, s), 7.90 (4H, s), 6.79–7.56 (5H, m), 4.95 (2H, s)

2) 2-[5-[(Hexahydro-1H-azepin-1-yl)methyl]-2-thienyl]imidazo(1,2-a]pyridine hydrochloride 2-[5-Phthalimidomethyl-2-thienyl]imidazo[1,2-a]pyridine (0.38 g) and hydrazine hydrate (0.058 g) were dissolved in a mixed solvent of methanol (10 ml) and chloroform (5 ml) and heated overnight under reflux. The reaction solution was filtered, and the resulting filtrate was concentrated and then purified by a silica gel column chromatography (chloroform:methanol=4:1) to give 0.14 g of an aminomethylthiophene intermediate. This intermediate (0.14 g) and 1,6-dibromohexane (0.16 g), potassium carbonate (0.19 g) and potassium iodide (0.05 g) were added to n-butanol (10 ml), and the mixture was heated under reflux for 6 hours. The reaction solution was filtered, the resulting filtrate was concentrated and purified by a silica gel column chromatography (chloroform:methanol=10:1) and then the purified product was converted into its salt with 4 N hydrochloric acid-ethyl acetate solution in ether, thereby obtaining 0.061 g of the title compound.

Melting point: 214–217° C. MS (FAB, Pos, m/z) 312 ($M^+$+1)

EXAMPLE 63

1) 2-[5-Phthalimidomethyl-2-thienyl]imidazo[1,2-a]pyrimidine

Using 2-aminopyrimidine, the title compound was obtained in the same manner as described in the step 1) of Example 62.

$^1$H-NMR (δ ppm in DMSO-$d_6$) 8.91 (1H, dd), 8.50 (1H, dd), 8.22 (1H, s), 7.90 (4H, d), 7.44 (1H, d), 7.00–7.13 (2H, m), 4.97 (2H, s)

2) 2-[5-[(Hexahydro-1H-azepin-1-yl)methyl]-2-thienyl imidazo[1,2-a]pyrimidine fumarate The title compound was synthesized in the same manner as described in the step 2) of Example 62, using 2-[5-phthalimidomethyl-2-thienyl]imidazo(1,2-a]pyrimidine as the starting material and carrying out the salt formation using fumaric acid.

Melting point: 188–191° C.

$^1$H-NMR (δ ppm in DMSO-$d_6$) 8.92 (1H, dd), 8.51 (1H, dd), 8.21 (1H, s), 7.43 (1H, d), 7.05 (1H, dd), 6.99 (1H, d), 6.59 (2H, s), 3.88 (2H, s), 2.50 (4H, brd), 1.59–1.66 (8H, br)

EXAMPLE 64

Ethyl 4-[5-[(hexahydro-1H-azepin-1-yl)methyl]-2-thienyl]benzoate

With ice-cooling, 3.8 ml of (1 N) diisobutyl aluminum hydride-toluene solution was added to 100 ml of anhydrous tetrahydrofuran solution of 2.5 g of bis(triphenylphosphine) nickel (II) chloride, and the mixture was stirred for 10 minutes and then 4.3 g of ethyl 4-iodobenzoate was added. Then, a solution prepared from 3.0 g of 1-(2-thienyl)hexahydro-1-azepine, 60 ml of anhydrous tetrahydrofuran, 9.6 ml of (1.6 N) n-butyl lithium-hexane solution and 5.4 ml of (1 N) zinc chloride ether solution was injected into the above mixture using a cannula at −78° C. under a pressure of argon gas, subsequently carrying out overnight stirring at room temperature. The reaction solution was filtered through celite, the resulting filtrate was concentrated under a reduced pressure, 100 ml of saturated sodium bicarbonate aqueous solution was added to the resulting residue, and the mixture was extracted three times with 100 ml of chloroform. The organic layers were combined, washed with saturated brine and concentrated under a reduced pressure. The resulting residue was purified by a silica gel column chromatography. Then, 4 N hydrochloric acid-ethyl acetate was added and the thus precipitated crystals were collected by filtration to give 290 mg (4%) of the title compound.

Melting point: 194–197° C.

$^1$H-NMR (δ ppm in DMSO-d$_6$) 1.34 (3H, t), 1.55–1.90 (8H, m), 3.10–3.20 (2H, m), 3.30–3.50 (2H, m), 4.33 (2H, q), 4.62 (2H, d), 7.92 (1H, d), 7.70 (1H, d), 7.82 (2H, d), 8.01 (2H, d), 9.85 (1H, br)

EXAMPLE 65

3-Amino-5-[5-[(pyrrolidin-1-yl)methyl]-2-thienyl]-1H-1,2,4-triazole

In the same manner as described in Example 38, 580 mg of the title compound was obtained from 1.8 g (7.99 mmol) of 2-(1-pyrrolidinyl)methylthiophene-5-carboxylic acid hydrazide.

Melting point: 180–181° C.

$^1$H-NMR (δ ppm in DMSO-d$_6$) 11.96 (1H, brs), 7.21 (1H, brs), 6.87 (1H, brs), 6.05 (2H, brs), 3.70 (2H, s), 2.51–2.48 (4H, m), 1.73–1.66 (4H, m)

EXAMPLE 66

1-[5-(5-Amino-1H-1,2,4-triazol-3-yl)-3-thenyl]hexahydro-1H-azepine

In the same manner as described in Example 38, 2.03 g of the title compound was obtained from 3.32 g (13.1 mmol) of 4-(hexahydro-1H-azepin-1-yl)methylthiophene-2-carboxylic acid hydrazide.

Melting point: 167–168° C.

$^1$H-NMR (δ ppm in DMSO-d$_6$) 12.02 (1H, br), 7.33 (1H, s), 7.18 (1H, s), 6.03 (2H, br), 3.56 (2H, s), 2.56–2.51 (4H, m), 1.55 (8H, s)

EXAMPLE 67

1-[2-[5-(5-Amino-1H-1,2,4-triazol-3-yl)-2-thienyl]ethyl]hexahydro-1H-azepine

In the same manner as described in Example 38, 2.39 g of the title compound was obtained from 3.70 g (13.84 mmol) of 5-[2-(hexahydro-1H-azepin-1-yl)ethyl]thiophene-2-carboxylic acid hydrazide.

Melting point: 109–110° C.

$^1$H-NMR (δ ppm in DMSO-d$_6$) 11.94 (1H, br), 7.18 (1H, s), 6.79 (1H, s), 6.00 (2H, br), 2.90–2.86 (2H, m), 2.70–2.62 (6H, m), 1.59–1.56 (8H, m)

EXAMPLE 68

3-Amino-5-[5-(1H-imidazol-1-ylmethyl)-2-thienyl]-1H-1,2,4-triazole

In the same manner as described in Example 38, 177 mg of the title compound was obtained from 360 mg (1.36 mmol) of 2-(1H-imidazol-1-yl)methylthiophene-5-carboxylic acid hydrazide.

Melting point: 178–180° C.

$^1$H-NMR (δ ppm in DMSO-d$_6$) 12.03 (1H, brs), 7.75 (1H, brs), 7.24 (1H, d), 7.22 (1H, brs), 7.03 (1H, d), 6.91 (1H, brs), 6.09 (2H, brs), 5.38 (2H, brs)

EXAMPLE 69

2-Amino-5-[5-(1H-imidazol-1-ylmethyl)-2-thienyl]-1,3,4-oxadiazole hydrobromide

In the same manner as described in Example 43, 866 mg of the title compound was obtained from 1.11 g (5.0 mmol) of 2-(1H-imidazol-1-yl)methylthiophene-5-carboxylic acid hydrazide.

Melting point: 261–262° C.

$^1$H-NMR (δ ppm in DMSO-d$_6$) 9.28 (1H, s), 7.86 (1H, s), 7.71 (1H, s), 7.43 (1H, s), 7.37–7.34 (3H, m), 5.77 (2H, brs)

EXAMPLE 70

N-[5-[5-[(Hexahydro-1H-azepin-1-yl)methyl]-2-thienyl]-1,3,4-oxadiazol-2-yl]benzamide hydrochloride 1.8 ml (15.0 mmol) of benzoyl chloride was added to 15 ml of pyridine solution containing 278 mg (1.0 mmol) of the compound of Example 43, and the mixture was stirred at 80° C. for 10 days. The reaction solution was concentrated under a reduced pressure, chloroform was added to the resulting residue, followed by washing with water and drying over anhydrous magnesium sulfate. The solvent was evaporated, the resulting residue was purified by a silica gel column chromatography. Then, the resulting crude crystals were recrystallized from ethanol-diisopropyl ether to give 241 mg of the title compound.

Melting point: 182–184° C.

$^1$H-NMR (δ ppm in DMSO-d$_6$) 12.23 (1H, br), 10.96 (1H, br), 8.04 (2H, d), 7.75 (1H, d), 7.68 (1H, t), 7.61–7.54 (3H, m), 4.65 (2H, s), 3.45–3.43 (2H, br), 3.10 (2H, br), 1.85 (4H, brs), 1.65 (4H, br)

EXAMPLE 71

1-[5-(5-Benzylamino-1,3,4-oxadiazol-2-yl)-2-thenyl]hexahydro-1H-azepine 0.13 ml (1.05 mmol) of benzyl isocyanate was added to 25 ml of acetonitrile solution containing 253 mg (1.0 mmol) of 2-(hexahydro-1H-azepin-1-yl)methylthiophene-5-carboxylic acid hydrazide, and the mixture was stirred at room temperature for 40 hours, 718 mg (2.2 mmol) of 1,2-dibromo-1,1,2,2-tetrachloroethane, 1.22 ml of triethylamine and 1.16 g of triphenylphosphine were added, and then the mixture was stirred at room temperature for 9 hours. The reaction solution was concentrated, chloroform was added to the resulting residue, followed by washing with water and drying over anhydrous magnesium sulfate. The solvent was evaporated and the resulting residue was purified by a silica gel column chromatography to give 122 mg of the title compound in its free form. By subjecting 117 mg of this compound to salt formation using 27 mg of oxalic acid, 122 mg of the title compound was obtained.

Melting point: 104–105° C.

$^1$H-NMR (δ ppm in DMSO-d$_6$) 8.42 (1H, t), 7.45 (1H, d), 7.38–7.26 (7H, m), 4.43 (2H, d), 4.32 (2H, br), 3.00 (4H, brs), 1.72 (4H, brs), 1.59 (4H, brs)

EXAMPLE 72

1-[5-(5-Hydroxy-1,3,4-oxadiazol-2-yl)-2-thenyl]hexahydro-1H-azepine 760 mg (3.0 mmol) of 2-(hexahydro-1H-azepin-1-yl)methylthiophene-5-carboxylic acid hydrazide was dissolved in 30 ml of tetrahydrofuran and 3 ml of N,N-dimethylformamide, 583 mg (3.6 mmol) of 1,1'-carbonyldiimidazole and 0.84 ml (6.0 mmol) of triethylamine were added, and the mixture was heated under reflux for 3 hours. The reaction solution was concentrated, chloroform was added to the resulting residue, followed by washing with water and drying over anhydrous magnesium sulfate. The solvent was evaporated and the resulting residue was purified by a silica gel column chromatography to give 793 mg of the title compound.

Melting point: 117–119° C.

$^1$H-NMR (δ ppm in CDCl$_3$) 8.84 (1H, br), 7.44 (1H, d), 6.91 (1H, d), 3.89 (2H, brs), 2.74–2.71 (4H, m), 1.74–1.58 (8H, m)

EXAMPLE 73

1-[5-[5-(2-Pyridyl)-1,3,4-oxadiazol-2-yl]-2-thenyl] hexahydro-1H-azepine oxalate 8 ml of pyridine and 1.28 g of picolinic acid chloride hydrochloride were added to 50 ml of dichloromethane solution containing 1,010 mg (4.0 mmol) of 2-(hexahydro-1H-azepin-1-yl)methylthiophene-5-carboxylic acid hydrazide, and the mixture was stirred overnight at room temperature. The reaction solution was washed with water and then dried over anhydrous magnesium sulfate. The solvent was evaporated and then the resulting residue was subjected to azeotropic treatment four times with 50 ml of toluene, thereby obtaining 1.5 g of crystals. A 268 mg (0.75 mmol) portion of the crystals was dissolved in 30 ml of dichloromethane, 0.23 ml of triethylamine and 140 mg (0.83 mmol) of 2-chloro-1,3-dimethylimidazolium chloride were added with ice-cooling, and the mixture was stirred at room temperature for 4 days. The reaction solution was washed with water and then dried over anhydrous magnesium sulfate. The solvent was evaporated and the resulting residue was purified by a silica gel column chromatography to give 87 mg of the title compound in its free form. By subjecting a 75 mg portion of this compound to salt formation using 19 mg of oxalic acid, 76 mg of the title compound was obtained.

Melting point: 217–218° C.

$^1$H-NMR (δ ppm in DMSO-d$_6$) 8.80 (1H, d), 8.25 (1H, d), 8.08 (1H, m), 7.86 (1H, d), 7.66 (1H, m), 7.33 (1H, brs), 4.29 (2H, brs), 1.72 (4H, brs), 1.61 (4H, brs)

EXAMPLE 74

1-[5-(5-Methyl-1,3,4-oxadiazol-2-yl)-2-thenyl] hexahydro-1H-azepine oxalate

Using 507 mg (2.0 mmol) of 2-(hexahydro-1H-azepin-1-yl)methylthiophene-5-carboxylic acid hydrazide and 0.23 ml (2.4 mmol) of acetic anhydride, 81 mg of the title compound was obtained in the same manner as described in Example 73.

Melting point: 91–92° C.

$^1$H-NMR (δ ppm in DMSO-d$_6$) 7.68 (1H, d), 7.28 (1H, d), 4.28 (2H, s), 2.56 (3H, s), 1.71 (4H, brs), 1.59 (6H, brs)

Example 75

1-[5-(5-Phenyl-1,3,4-oxadiazol-2-yl)-2-thenyl] hexahydro-1H-azepine 687 mg (4.0 mmol) of methylbenzoimidate hydrochloride was added to 7 ml of pyridine solution containing 507 mg (2.0 mmol) of 2-(hexahydro-1H-azepin-1-yl) methylthiophene- 5-carboxylic acid hydrazide, and the mixture was heated under reflux for 4 hours. The reaction solution was concentrated, chloroform was added to the resulting residue, followed by washing with water and drying over anhydrous magnesium sulfate. The solvent was evaporated and the resulting residue was purified by a silica gel column chromatography to give 110 mg of the title compound.

Melting point: 95–97° C.

$^1$H-NMR (δ ppm in CDCl$_3$) 8.13–8.10 (2H, m), 7.68 (1H, d), 7.56–7.50 (4H, m), 3.89 (2H, s), 2.72–2.70 (4H, m), 1.73–1.60 (8H, m)

EXAMPLE 76

N-Benzyl-5-[5-[(hexahydro-1H-azepin-1-yl)methyl]-2-thienyl]-1H-1,2,4-triazole-3-carboxamide 1.0 g (3.0 mmol) of the compound obtained in Example 40 was dissolved in 3.3 ml (30.0 mmol) of benzylamine, and the solution was stirred at 80° C. for 4 hours. Chloroform was added to the resulting residue, followed by washing with water and drying over anhydrous magnesium sulfate. The solvent was evaporated, the resulting residue was purified by a silica gel column chromatography. The resulting crystals were washed with hot diisopropyl ether and recrystallized from ethyl acetate-n-hexane to give 997 mg of the title compound.

Melting point: 137–139° C.

$^1$H-NMR (δ ppm in DMSO-d$_6$) 9.20 (1H, br), 7.53 (1H, d), 7.34 (5H, br), 7.25 (1H, t), 6.99 (1H, d), 4.48 (2H, d), 3.82 (2H, s), 2.61 (4H, brs), 1.54 (8H, brs)

EXAMPLE 77

N-Benzyl-5-[5-[(hexahydro-1H-azepin-1-yl)methyl]-2-thienyl]-1H-1,2,4-triazol-3-ylmethylamine 3/2 fumarate 10 ml of anhydrous tetrahydrofuran solution containing 594 mg (1.5 mmol) of the compound obtained in Example 76 was added dropwise to 5 ml of anhydrous tetrahydrofuran suspension containing 230 mg (6.0 mmol) of lithium aluminum hydride, and the mixture was heated under reflux for 11 hours. Then, 460 mg (12.0 mmol) of lithium aluminum hydride was added and the mixture was again heated under reflux for 3 days. To the reaction mixture was added sodium sulfate decahydrate, the resulting insoluble matter was removed by filtration. The solvent was evaporated and then the resulting residue was purified by a silica gel column chromatography to give 104 mg of the title compound in its free form. By subjecting a 74 mg portion of this compound to salt formation using 33 mg of fumaric acid and recrystallizing it from methanol, 63 mg of the title compound was obtained.

Melting point: 155–157° C.

$^1$H-NMR (δ ppm in DMSO-d$_6$) 7.42–7.32 (5H, m), 7.26 (1H, m), 6.97 (1H, brs), 6.60 (3H, s), 3.86–3.84 (4H, m), 3.80 (2H, brs), 2.68–2.66 (4H, m), 1.58 (8H, brs)

EXAMPLE 78

[5-[5-[(Hexahydro-1H-azepin-1-yl)methyl]-2-thienyl]-1H-1,2,4-triazol-3-yl]methyl benzoate In the same manner as described in Example 6, 351 mg of the title compound was obtained from 292 mg (1.0 mmol) of the compound of Example 41.

FAB MS (Pos, m/z) 397 (M$^+$+1)

$^1$H-NMR (δ ppm in CDCl$_3$) 8.04 (2H, d), 7.56 (1H, t), 7.50 (1H, d), 7.41 (3H, t), 6.87 (1H, d), 5.49 (2H, s), 3.87 (2H, s), 2.74–2.66 (4H, m), 1.70–1.54 (8H, m)

EXAMPLE 79

1-[5-[5-(2-Pyridyl)-1H-1,2,4-triazol-3-yl]-2-thenyl)hexahydro-1H-azepine 81 mg (1.5 mmol) of sodium methoxide was added to 13.5 ml of methanol solution containing 1.56 g (15.0 mmol) of 2-cyanopyridine and stirred at room temperature for 3.5 hours. The reaction mixture was ice-cooled, 0.085 ml (1.5 mmol) of acetic acid and 1.52 g (6.0 mmol) of 2-(hexahydro-1H-azepin-1-yl)methylthiophene-5-carboxylic acid hydrazide were added with ice-cooling, and then the mixture was stirred at room temperature for 24 hours. The thus precipitated crystals were collected by filtration to give 1.97 g of the crystals. A 894 mg (2.5 mmol) portion of them was dissolved in 13 ml of acetic acid and heated under reflux for 6.5 hours. The solvent was evaporated, 28% aqueous ammonia and chloroform were added, and then the thus separated organic layer was dried over anhydrous magnesium sulfate. The solvent was evaporated and the resulting residue was purified by a silica gel column chromatography to give 715 mg of the title compound.

Melting point: 160–162° C.

$^1$H-NMR (δ ppm in DMSO-$d_6$) 14.74 (1H, br), 8.72 (1H, d), 8.12 (1H, d), 8.01 (1H, dt), 7.54 (1H, m), 7.50 (1H, d), 6.98 (1H, d), 3.83 (2H, s), 2.68–2.60 (4H, m), 1.58 (8H, brs)

EXAMPLE 80

1-(5-(2-Methyl-2H-1,2,4-triazol-3-yl)-2-thenyl]hexahydro-1H-azepine hydrochloride 0.3 ml (5.59 mmol) of methylhydrazine was added dropwise to 6.5 ml of acetic acid solution containing 820 mg (2.8 mmol) of the compound obtained in the step 1) of Example 53, and the mixture was heated under reflux for 5 days. Then, 0.6 ml (11.18 mmol) of methylhydrazine was added and the mixture was again heated under reflux for 2 days. The solvent was evaporated, 28% aqueous ammonia and chloroform were added, and then the resulting organic layer was separated and washed with saturated brine and dried over anhydrous magnesium sulfate. The solvent was evaporated, and the resulting residue was purified by a silica gel column chromatography, subjected to salt formation using 0.7 ml of 4 N HCl/ethyl acetate and then recrystallized from acetonitrile, thereby obtaining 204 mg of the title compound.

Melting point: 232–233° C.

$^1$H-NMR (δ ppm in DMSO-$d_6$) 10.61 (1H, br), 8.00 (1H, d), 7.69 (1H, d), 7.54 (1H, d), 4.61 (2H, brs), 4.07 (3H, s), 3.40–3.34 (2H, m), 3.13–3.05 (2H, m), 1.83 (4H, brs), 1.66–1.58 (4H, m)

EXAMPLE 81

1-[5-(3-(2-Pyridyl)-1,2,4-oxadiazol-5-yl)-2-thenyl]hexahydro-1H-azepine oxalate

Using 1.07 g (4.0 mmol) of ethyl 5-[(hexahydro-1H-azepin-1-yl)methyl-2-thienyl]carboxylate and 823 mg (6.0 mmol) of 2-pyridylamdoxime, 149 mg of the title compound was obtained in its free form in the same manner as described in Example 1. By subjecting 72 mg of this compound to salt formation using 18 mg of oxalic acid, 57 mg of the title compound was obtained.

Melting point: 164–166° C.

$^1$H-NMR (δ ppm in DMSO-$d_6$) 8.79 (1H, d), 8.14 (1H, d), 8.08–8.03 (2H, m), 7.64 (1H, m), 7.40 (1H, d), 4.34 (2H, s), 2.98 (4H, br), 1.73 (4H, brs), 1.61 (4H, brs)

EXAMPLE 82

1) O-[5-(Hexahydro-1H-azepin-1-yl)methyl-2-thenoyl]-3-phthalimidopropionamidoxime 9.59 g (93.0 mM) of 3-aminopropionamidoxime was dissolved in 288 ml of 1,3-dimethyl-2-imidazolidinone, 14.46 g (97.65 mM) of phthalic anhydride was added, and the mixture was stirred at room temperature for 1 hour and then at 140° C. for 2 hours. The reaction solution was cooled to room temperature, and 15.6 ml (111.6 mM) of triethylamine and 16.4 g (55.8 mM) of 5-(hexahydro-1H-azepin-1-yl)methyl-2-thiophene carbonylchloride hydrochloride were added. The mixture was stirred -overnight at room temperature, and 720 ml of saturated brine was added. Then, the thus precipitated crystals were collected by filtration and washed with distilled water to give 19.96 g of O-[5-(hexahydro-1H-azepin-1-yl)methyl-2-thenoyl]-3-phthalimidopropionamidoxime (79% in yield from (hexahydro-1H-azepin-1-yl)methyl-2-thiophene carbonylchloride hydrochloride).

$^1$H-NMR (δ ppm in DMSO-$d_6$) 7.85 (4H, s), 7.00 (1H, d), 6.57 (1H, d), 3.82 (2H, s), 2.51 (4H, br), 1.56 (8H, brs)

2) N-[2-[5-[5-[(Hexahydro-1H-azepin-1-yl)methyl]-2-thienyl]-1,2,4-oxadiazol-3-yl]ethyl]phthalimide hydrochloride To 2.57 g of O-[5-(hexahydro-1H-azepin-1-yl)methyl-2-thenoyl]-3-phthalimidopropionamidoxime was added 100 ml of xylene, and the mixtures was heated under reflux for 8 hours. The reaction solution was cooled to room temperature, filtered and, with ice-cooling, 2 ml of 4 N hydrochloric acid/ethyl acetate was added. Then, the thus precipitated crystals were collected by filtration to give 2.2 g (82% in yield) of the title compound.

EXAMPLE 83

1-[5-(5-Amino-1H-1,2,4-triazol-3-yl)-2-thenyl]hexahydro-1H-azepine 500 ml of 1,3-dimethyl-2-imidazolidinone and 18.0 g (163.2 mM) of aminoguanidine hydrochloride were added to 24.0 g (81.6 mM) of 5-(hexahydro-1H-azepin-1-yl)methyl-2-thiophenecarbonyl chloride, and the mixture was stirred at room temperature for 1 hour. Then, 16.3 g (60% oil, 408 mM) was added and the mixture was stirred overnight at 130° C. The reaction solution was cooled to room temperature, 50 ml of water and 500 ml of n-hexane were added to effect separation of layers. To the resulting lower layer was added 1,000 ml of saturated brine, and then the mixture was extracted seven times with 500 ml of ethyl acetate. The ethyl acetate layer was dried over anhydrous sodium sulfate, concentrated under a reduced pressure, and 1,000 ml of acetonitrile was added. With ice-cooling, 150 ml of 4 N hydrochloric acid/ethyl acetate was added, and the thus precipitated crystals were collected by filtration. The resulting crystals were added to 200 ml of 1 N sodium hydroxide, extracted three times with 200 ml of ethyl acetate, dried over anhydrous sodium sulfate and then concentrated to ¹/₁₀ volume under a reduced pressure. The thus precipitated crystals were collected by filtration to give 10.4 g (51% in yield) of the title compound.

The following table shows chemical structures of the compounds obtained in Examples 1 to 83.

| Example | Chemical Structural Formula |
|---------|----------------------------|
| 1 | azepane-CH₂-thiophene-(1,2,4-oxadiazole)-CH₂-phenyl |
| 2 | azepane-CH₂-thiophene-(1,2,4-oxadiazole)-(CH₂)₂-phenyl |
| 3 | azepane-CH₂-thiophene-(1,2,4-oxadiazole)-(CH₂)₃-phenyl |
| 4 | azepane-CH₂-thiophene-(1,2,4-oxadiazole)-CH₂OH |
| 5 | azepane-CH₂-thiophene-(1,2,4-oxadiazole)-CH₂-O-CH₂-phenyl |
| 6 | azepane-CH₂-thiophene-(1,2,4-oxadiazole)-CH₂-O-C(=O)-phenyl |
| 7 | azepane-CH₂-thiophene-(1,2,4-oxadiazole)-CH₂-O-C(=O)-NH-CH₂-phenyl |
| 8 | azepane-CH₂-thiophene-(1,2,4-oxadiazole)-CH₂-NH₂ |

-continued

| Example | Chemical Structural Formula |
|---------|----------------------------|
| 9 | |
| 10 | |
| 11a) | |
| 11b) | |
| 12 | |
| 13 | |
| 14 | |
| 15 | |

-continued

| Example | Chemical Structural Formula |
|---|---|
| 16 | |
| 17 | |
| 18 | |
| 19 | |
| 20 | |
| 21 | |
| 22 | |
| 23 | |
| 24 | |

-continued
| Example | Chemical Structural Formula |
|---|---|
| 25 | 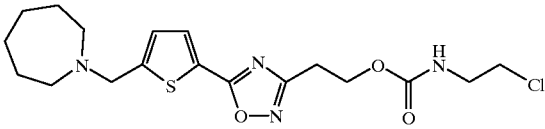 |
| 26 | 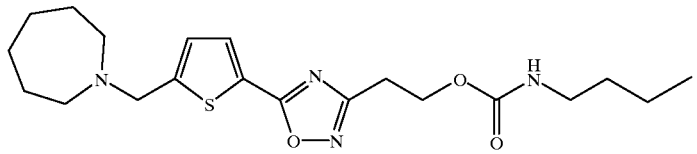 |
| 27 | 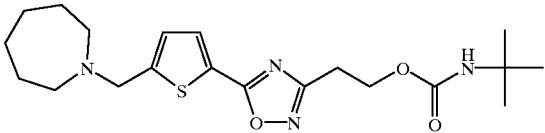 |
| 28 | 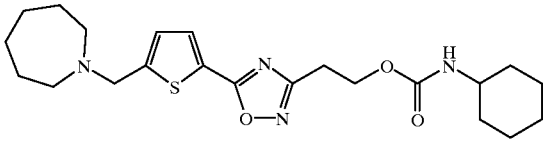 |
| 29 | 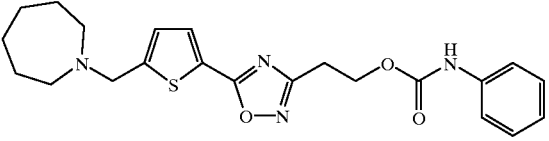 |
| 30 | 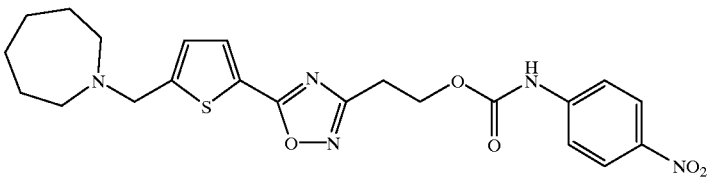 |
| 31 | 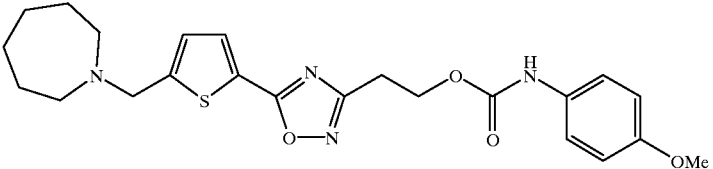 |
| 32 | 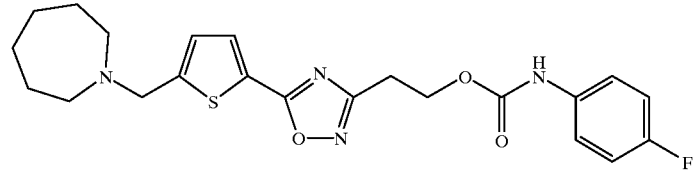 |
| 33 | 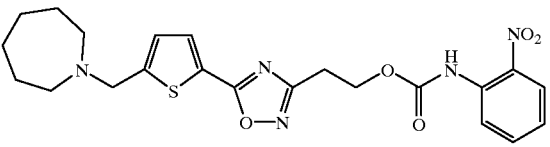 |

-continued
| Example | Chemical Structural Formula |
|---|---|
| 34 | 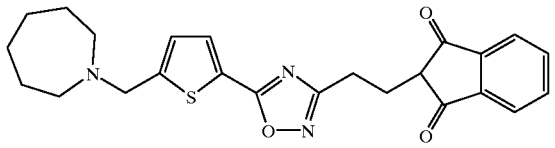 |
| 35 | 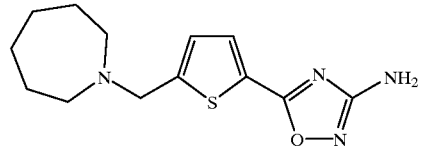 |
| 36 | 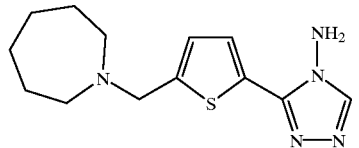 |
| 37 | 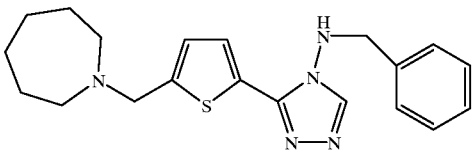 |
| 38 | 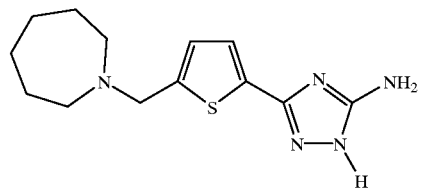 |
| 39 | 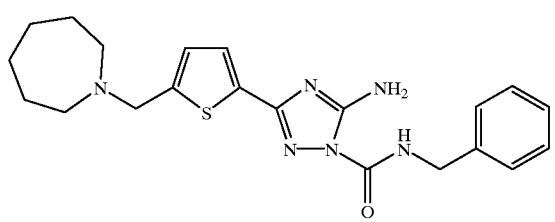 |
| 40 | 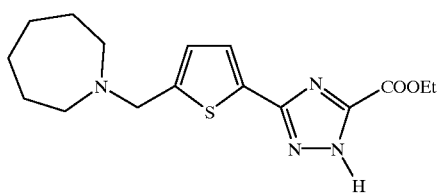 |
| 41 | 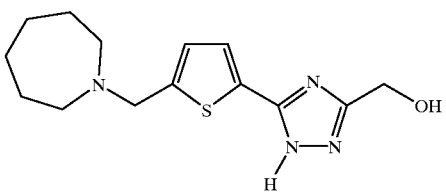 |

-continued

| Example | Chemical Structural Formula |
|---|---|
| 42 | (azepan-1-yl)methyl-thiophene-3-(5-methyl-1H-1,2,4-triazole) |
| 43 | (azepan-1-yl)methyl-thiophene-2-(5-amino-1,3,4-oxadiazole) |
| 44 | (azepan-1-yl)methyl-thiophene-2-(1,3,4-oxadiazol-2-yl)-N-benzylurea |
| 45 | (azepan-1-yl)methyl-thiophene-2-(5-amino-1,3,4-thiadiazole) |
| 46 | (azepan-1-yl)methyl-thiophene-2-(1,3,4-thiadiazol-2-yl)-N-benzylurea |
| 47 | (azepan-1-yl)methyl-thiophene-2-(1,3,4-thiadiazol-2-yl)-N-benzamide |
| 48 | (azepan-1-yl)methyl-thiophene-2-(5-benzylamino-1,3,4-thiadiazole) |
| 49 | (azepan-1-yl)methyl-thiophene-2-(5-ethylamino-1,3,4-thiadiazole) |
| 50 | (azepan-1-yl)methyl-thiophene-2-(1,3,4-thiadiazol-2-yl)-N-ethylurea |

| Example | Chemical Structural Formula |
|---------|----------------------------|
| 51 | |
| 52 | |
| 53 | |
| 54 | |
| 55 | |
| 56 | |
| 57 | |
| 58 | |

-continued

| Example | Chemical Structural Formula |
|---|---|
| 59 | (azepane)-CH2-(thiophene)-(1,2,4-oxadiazole)-CH2CH2OH |
| 60 | (azepane)-CH2-(thiophene)-(1,2,4-oxadiazole)-CH2CH2NH2 |
| 61 | (azepane)-CH2-(thiophene)-(4-methylthiazole) |
| 62 | (azepane)-CH2-(thiophene)-(imidazo[1,2-a]pyridine) |
| 63 | (azepane)-CH2-(thiophene)-(imidazo[1,2-a]pyrimidine) |
| 64 | (azepane)-CH2-(thiophene)-(phenyl)-COOEt |
| 65 | (pyrrolidine)-CH2-(thiophene)-(1,2,4-triazole)-NH2 |
| 66 | (azepane)-CH2-(thiophene, 3,4-substituted)-(1,2,4-triazole)-NH2 |

-continued

| Example | Chemical Structural Formula |
|---|---|
| 67 | (azepane)-CH₂CH₂-(thiophene)-(1,2,4-triazole)-NH₂ |
| 68 | (imidazole)-CH₂-(thiophene)-(1,2,4-triazole)-NH₂ |
| 69 | (imidazole)-CH₂-(thiophene)-(1,3,4-oxadiazole)-NH₂ |
| 70 | (azepane)-CH₂-(thiophene)-(1,3,4-oxadiazole)-NH-C(=O)-phenyl |
| 71 | (azepane)-CH₂-(thiophene)-(1,3,4-oxadiazole)-NH-CH₂-phenyl |
| 72 | (azepane)-CH₂-(thiophene)-(1,3,4-oxadiazole)-OH |
| 73 | (azepane)-CH₂-(thiophene)-(1,3,4-oxadiazole)-(2-pyridyl) |
| 74 | (azepane)-CH₂-(thiophene)-(1,3,4-oxadiazole)-CH₃ |
| 75 | (azepane)-CH₂-(thiophene)-(1,3,4-oxadiazole)-phenyl |

-continued

| Example | Chemical Structural Formula |
|---|---|
| 76 | |
| 77 | |
| 78 | |
| 79 | |
| 80 | |
| 81 | |
| 82 | |

| Example | Chemical Structural Formula |
|---|---|
| 83 | 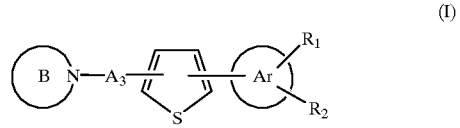 |

In addition to the aforementioned illustrative compounds, the following compounds can be synthesized without requiring particular experiments, in accordance with the aforementioned production methods, the methods described in examples or modified methods thereof, or other methods or their modifications known to those skilled in the art.

5-Benzylamino-3-[5-[(hexahydro-1H-azepin-1-yl)methyl]-2-thienyl]-1H-1,2,4-triazole
5-amino-3-[5-[(hexahydro-1H-azepin-1-yl)methyl]-2-thienyl]-1H-1,2,4-thiadiazole
5-Benzylureido-3-[5-[(hexahydro-1H-azepin-1-yl)methyl]-2-thienyl]-1H-1,2,4-thiadiazole
5-Benzoylamino-3-[5-[(hexahydro-1H-azepin-1-yl)methyl]-2-thienyl]-1H-1,2,4-thiadiazole
5-Benzylamino-3-[5-[(hexahydro-1H-azepin-1-yl)methyl]-2-thienyl]-1H-1,2,4-thiadiazole
5-Aminomethyl-3-[5-[(hexahydro-1H-azepin-1-yl)methyl]-2-thienyl]-1H-1,2,4-triazole
5-Phthalimidoylmethyl-3-[5-[(hexahydro-1H-azepin-1-yl)methyl]-2-thienyl]-1H-1,2,4-triazole
3-Benzylureido-5-[5-[(hexahydro-1H-azepin-1-yl)methyl]-2-thienyl]-1,2,4-oxadiazole
3-Benzylamino-5-[5-[(hexahydro-1H-azepin-1-yl)methyl]-2-thienyl]-1,2,4-oxadiazole
2-Benzoylamino-5-[5-[(hexahydro-1H-azepin-1-yl)methyl]-2-thienyl]-1,3,4-oxadiazole
2-Benzylamino-5-[5-[(hexahydro-1H-azepin-1-yl)methyl]-2-thienyl]-1,3,4-oxadiazole
4-Benzylureido-3-[5-[(hexahydro-1H-azepin-1-yl)methyl]-2-thienyl]-1H-1,2,4-triazole
4-Benzoylamino-3-[5-[(hexahydro-1H-azepin-1-yl)methyl]-2-thienyl]-1H-1,2,4-triazole
5-Benzylureido-3-[5-[(hexahydro-1H-azepin-1-yl)methyl]-2-thienyl]-1H-1,2,4-triazole
5-Benzoylamino-3-[5-[(hexahydro-1H-azepin-1-yl)methyl]-2-thienyl]-1H-1,2,4-triazole
1-Benzyl-3-[[3-[5-[(hexahydro-1H-azepin-1-yl)methyl]-2-thienyl]-1H-1,2,4-triazol-5-yl]methyl]urea
5-Benzoylaminomethyl-3-[5-[(hexahydro-1H-azepin-1-yl)methyl]-2-thienyl]-1H-1,2,4-triazole
5-Benzyloxymethyl-3-[5-[(hexahydro-1H-azepin-1-yl)methyl]-2-thienyl]-1H-1,2,4-triazole
5-Benzyloxymethyl-3-[5-[(hexahydro-1H-azepin-1-yl)methyl]-2-thienyl]-1H-1,2,4-triazole
5-Benzoyloxymethyl-3-[5-[(hexahydro-1H-azepin-1-yl)methyl]-2-thienyl]-1H-1,2,4-triazole
[3-[5-[(hexahydro-1H-azepin-1-yl)methyl]-2-thienyl]-1H-1,2,4-triazol-5-yl]methyl n-benzylcarbamate
5-Amino-3-[5-[(pyrrolidin-1-yl)methyl]-2-thienyl]-1H-1,2,4-triazole
5-amino-3-[4-[(hexahydro-1H-azepin-1-yl)methyl)-2-thienyl]-1H-1,2,4-triazole
1-[5-(2-Pyridyl)-2-thenyl]hexahydro-1H-azepine
1-[5-(2-Furyl)-2-thenyl]hexahydro-1H-azepine
1-[5-(2-Pyrimidyl)-2-thenyl]hexahydro-1H-azepine
1-[5-(4-Amino-2-pyridyl)-2-thenyl]hexahydro-1H-azepine
1-[5-(4-Aminophenyl)-2-thenyl]hexahydro-1H-azepine
5-Amino-3-[5-(hexahydro-1H-azepin-1-yl)methyl-2-thienyl]-1,2,4-oxadiazole
2-amino-4-[5-(hexahydroazepinyl)methyl-2-thienyl]imidazole

What is claimed is:

1. A thiophene derivative represented by the following general formula (I) or a pharmaceutically acceptable salt thereof

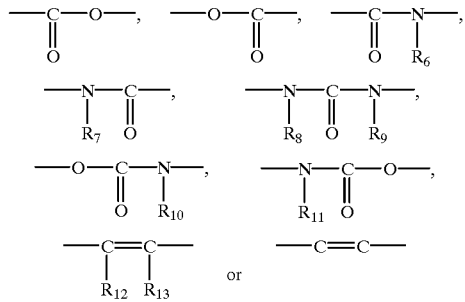

(I)

each symbol in the above formula is defined as follows:
$R_1$: formula $-A_1-X_1-R_3$,
$R_2$: formula $-A_2-X_2-R_4$ or is absent,
B ring: 7- to 10-membered nitrogen-containing cycloalkyl ring,
Ar ring: an aryl ring which may have a substituent, or a 5- or 6-membered aromatic heterocycle or an 8- to 10-membered aromatic bicyclic heterocycle, which contains 1 to 4 of one or more hetero atoms selected from the group consisting of a nitrogen atom, an oxygen atom and a sulfur atom,
$A_1$, $A_2$ and $A_3$: the same or different from one another, and each represents a bond or a lower alkylene group,
$X_1$ and $X_2$: the same or different from each other, and each represents a bond or a formula $-O-$, $-S-$, $-NR_5-$, $$-\overset{\text{O}}{\underset{\|}{C}}-O-, \quad -O-\overset{\text{O}}{\underset{\|}{C}}-, \quad -\overset{\text{O}}{\underset{\|}{C}}-\overset{\text{}}{\underset{R_6}{N}}-,$$

$$-\overset{\text{}}{\underset{R_7}{N}}-\overset{\text{O}}{\underset{\|}{C}}-, \quad -\overset{\text{}}{\underset{R_8}{N}}-\overset{\text{O}}{\underset{\|}{C}}-\overset{\text{}}{\underset{R_9}{N}}-,$$

$$-O-\overset{\text{O}}{\underset{\|}{C}}-\overset{\text{}}{\underset{R_{10}}{N}}-, \quad -\overset{\text{}}{\underset{R_{11}}{N}}-\overset{\text{O}}{\underset{\|}{C}}-O-,$$

$$-\overset{\text{}}{\underset{R_{12}}{C}}=\overset{\text{}}{\underset{R_{13}}{C}}- \quad \text{or} \quad -C\equiv C-$$

$R_5$, $R_6$, $R_7$, $R_8$, $R_9$, $R_{10}$, $R_{11}$, $R_{12}$ and $R_{13}$: the same or different from one another, and each represents a hydrogen atom or a lower alkyl group, and
$R_3$ and $R_4$: the same or different from each other, and each represents a hydrogen atom, a cyclic imido group which may have a substituent and may be condensed with a benzene ring, or a lower alkyl group, a cycloalkyl group, an aryl group or an aralkyl group, each of which may have a substituent, with the proviso that, when the Ar ring is a thiazole ring, either one of $A_1$ and $A_2$ is a lower alkylene group, when the Ar ring is a thiophene ring, at least one of $R_3$ and $R_4$ is a group other than a hydrogen atom, and when the Ar ring is a benzene ring, a case in which $R_1$ and $R_2$ is a methyl group or a halogen atom and the other is a hydrogen atom is excluded.

2. The thiophene derivative or a pharmaceutically acceptable salt thereof according to claim 1, wherein the B ring is a 7- to 10-membered nitrogen-containing cycloalkyl ring.

3. The thiophene derivative or a pharmaceutically acceptable salt thereof according to claim 1, wherein the B ring is a hexahydroazepine ring.

4. The thiophene derivative or a pharmaceutically acceptable salt thereof according to claim 1, wherein $A_3$ is a methylene group.

5. The thiophene derivative or a pharmaceutically acceptable salt thereof according to claim 1, wherein the Ar ring is a 5-membered aromatic heterocycle which contains 2 or 3 of one or more hetero atoms selected from the group consisting of a nitrogen atom, an oxygen atom and a sulfur atom or a 9-membered aromatic heterocycle which contains 2 to 4 of one or more hetero atoms selected from the group consisting of a nitrogen atom, an oxygen atom and a sulfur atom.

6. The thiophene derivative or a pharmaceutically acceptable salt thereof according to any one of claim 1, wherein the Ar ring is triazole, oxadiazole, thiazole, thiadiazole, imidazopyridine, imidazopyrimidine or triazolopyridazine.

7. 5-[5-[(Hexahydro-1H-azepin-1-yl)methyl]-2-thienyl]-3-phthalimidoylethyl-1,2,4-oxadiazole, 5-amino-3-[5-((hexahydro-1H-azepin-1-yl)methyl]-2-thienyl]-1H-1,2,4-triazole or a pharmaceutically acceptable salt thereof.

8. A pharmaceutical composition which comprises the thiophene derivative or a pharmaceutically acceptable salt thereof described in claim 1 and a pharmaceutically acceptable carrier.

9. The pharmaceutical composition according to claim 8, which is an anti-PCP agonist.

10. The pharmaceutical composition according to claim 9, wherein the anti-PCP agonist is a psychotropic agent or an antischizophrenic agent.

11. The pharmaceutical composition according to claim 9, wherein the anti-PCP agonist is a drug for preventing dementia, a drug for improving problematic behavior accompanied by dementia, a drug for treating mental retardation in childhood and/or a drug for treating autism.

* * * * *